(12) United States Patent
Edelhauser et al.

(10) Patent No.: US 10,888,260 B2
(45) Date of Patent: Jan. 12, 2021

(54) BIOLOGICAL FLUID COLLECTION DEVICE

(71) Applicant: Becton, Dickinson and Company, Franklin Lakes, NJ (US)

(72) Inventors: Adam Edelhauser, Kinnelon, NJ (US); Anthony V. Torris, Montclair, NJ (US); Robert G. Ellis, Wayne, NJ (US); Bradley M. Wilkinson, North Haledon, NJ (US); Joseph Nathan Pratt, Dunedin, FL (US); Bartosz Marek Korec, Palm Harbor, FL (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 424 days.

(21) Appl. No.: 15/187,001

(22) Filed: Jun. 20, 2016

(65) Prior Publication Data

US 2016/0367177 A1    Dec. 22, 2016

Related U.S. Application Data

(60) Provisional application No. 62/181,978, filed on Jun. 19, 2015.

(51) Int. Cl.
*B01L 3/00* (2006.01)
*A61B 5/15* (2006.01)
*A61B 5/153* (2006.01)

(52) U.S. Cl.
CPC .... *A61B 5/150755* (2013.01); *A61B 5/15003* (2013.01); *A61B 5/153* (2013.01); *A61B 5/150022* (2013.01); *A61B 5/15074* (2013.01); *A61B 5/150099* (2013.01); *A61B 5/150213* (2013.01); *A61B 5/150221* (2013.01); *A61B 5/150343* (2013.01); *B01L 3/502* (2013.01); *A61B 5/150351* (2013.01); *B01L 2200/0684* (2013.01); *B01L 2200/0689* (2013.01); *B01L 2400/049* (2013.01)

(58) Field of Classification Search
CPC ............ B01L 3/5027; B01L 3/502723; B01L 2200/0684; B01L 2300/044; B01L 2200/0689; A61B 5/150221; A61B 5/150755

See application file for complete search history.

(56) References Cited

U.S. PATENT DOCUMENTS

| | | | |
|---|---|---|---|
| 5,054,499 | A | 10/1991 | Swierczek |
| 5,636,640 | A | 6/1997 | Staehlin |
| 6,562,014 | B2 | 5/2003 | Lin et al. |
| 6,607,495 | B1 | 8/2003 | Skalak et al. |
| 7,335,166 | B2 | 2/2008 | Faupel et al. |
| 2008/0194986 | A1 | 8/2008 | Conway et al. |
| 2011/0172508 | A1 | 7/2011 | Chickering, III et al. |
| 2012/0016308 | A1 | 1/2012 | Schott |

(Continued)

FOREIGN PATENT DOCUMENTS

| | | |
|---|---|---|
| JP | 10000188 A | 1/1998 |
| JP | 2009247491 A | 10/2009 |

(Continued)

*Primary Examiner* — Jill A Warden
*Assistant Examiner* — Dwayne K Handy
(74) *Attorney, Agent, or Firm* — The Webb Law Firm

(57) ABSTRACT

A biological fluid collection device that allows a blood sample to be collected anaerobically is disclosed.

9 Claims, 24 Drawing Sheets

(56) References Cited

U.S. PATENT DOCUMENTS

| | | |
|---|---|---|
| 2014/0305197 A1 | 10/2014 | Fletcher et al. |
| 2014/0309551 A1 | 10/2014 | Burkholz et al. |
| 2014/0356941 A1* | 12/2014 | Bransky ............ B01L 3/502715 435/306.1 |

FOREIGN PATENT DOCUMENTS

| | | |
|---|---|---|
| JP | 2013538069 A | 10/2013 |
| WO | 9202175 A1 | 2/1992 |
| WO | 0078212 A1 | 12/2000 |
| WO | 0143643 A1 | 6/2001 |
| WO | 03099123 A1 | 12/2003 |
| WO | 2014172232 A1 | 10/2014 |
| WO | 2014172244 A1 | 10/2014 |

* cited by examiner

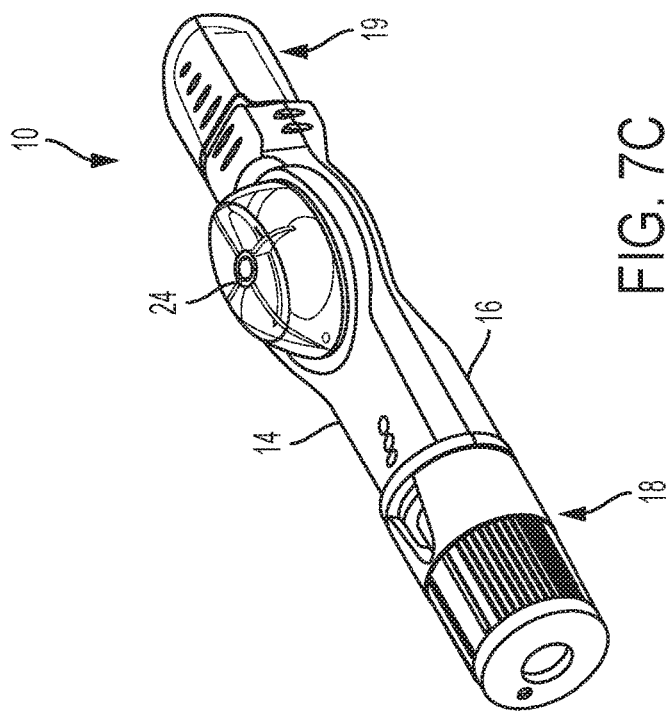
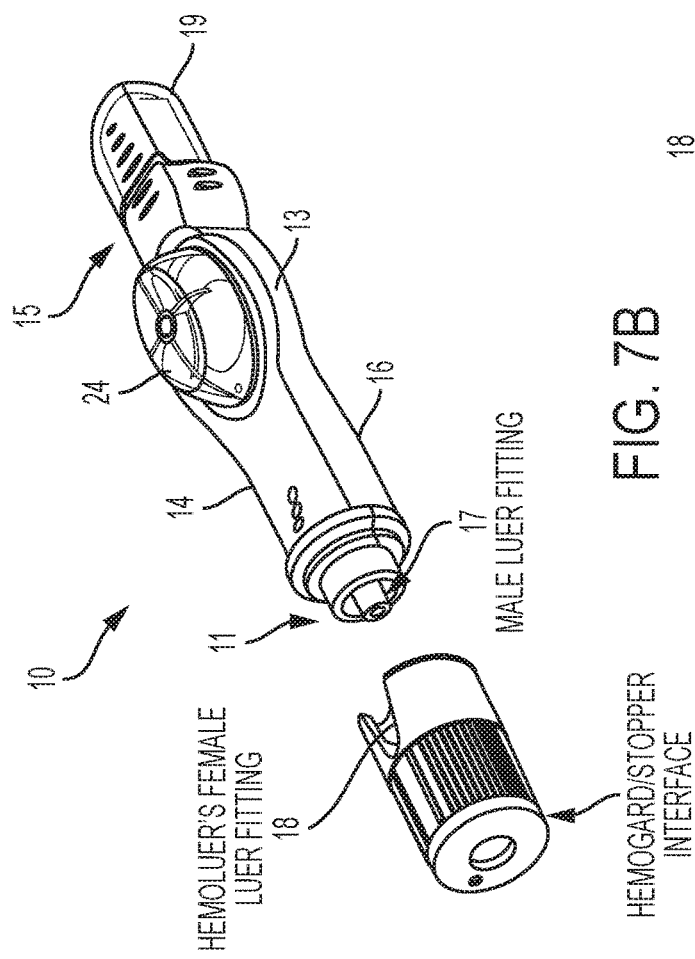
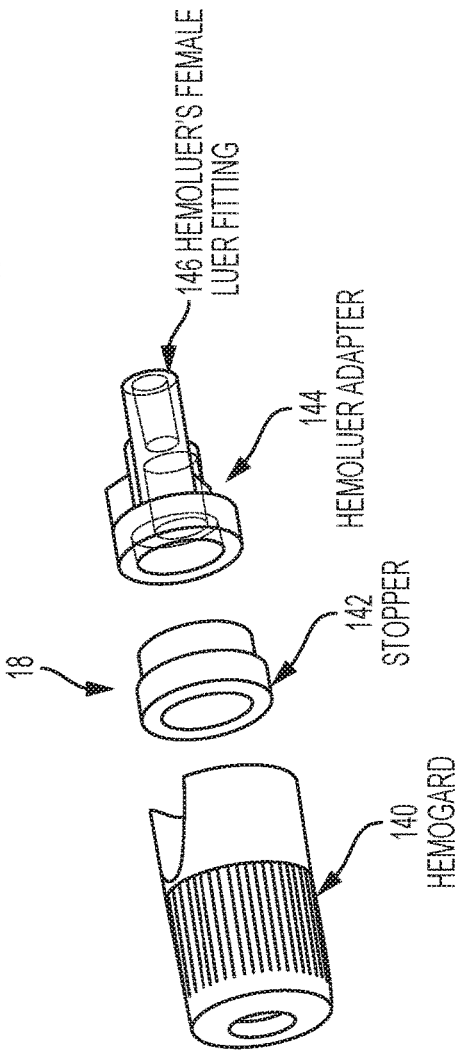
FIG. 7A
FIG. 7B
FIG. 7C

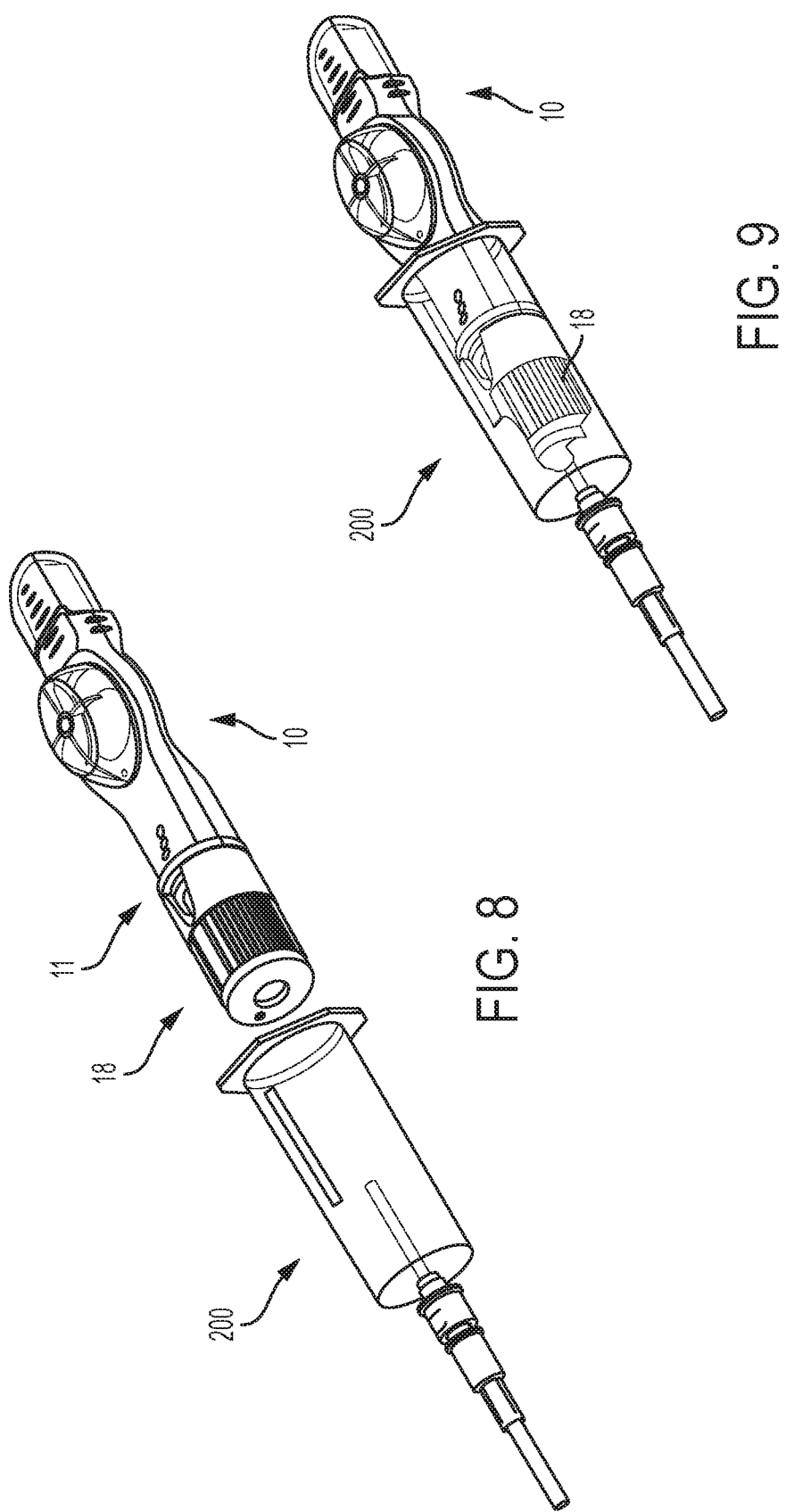

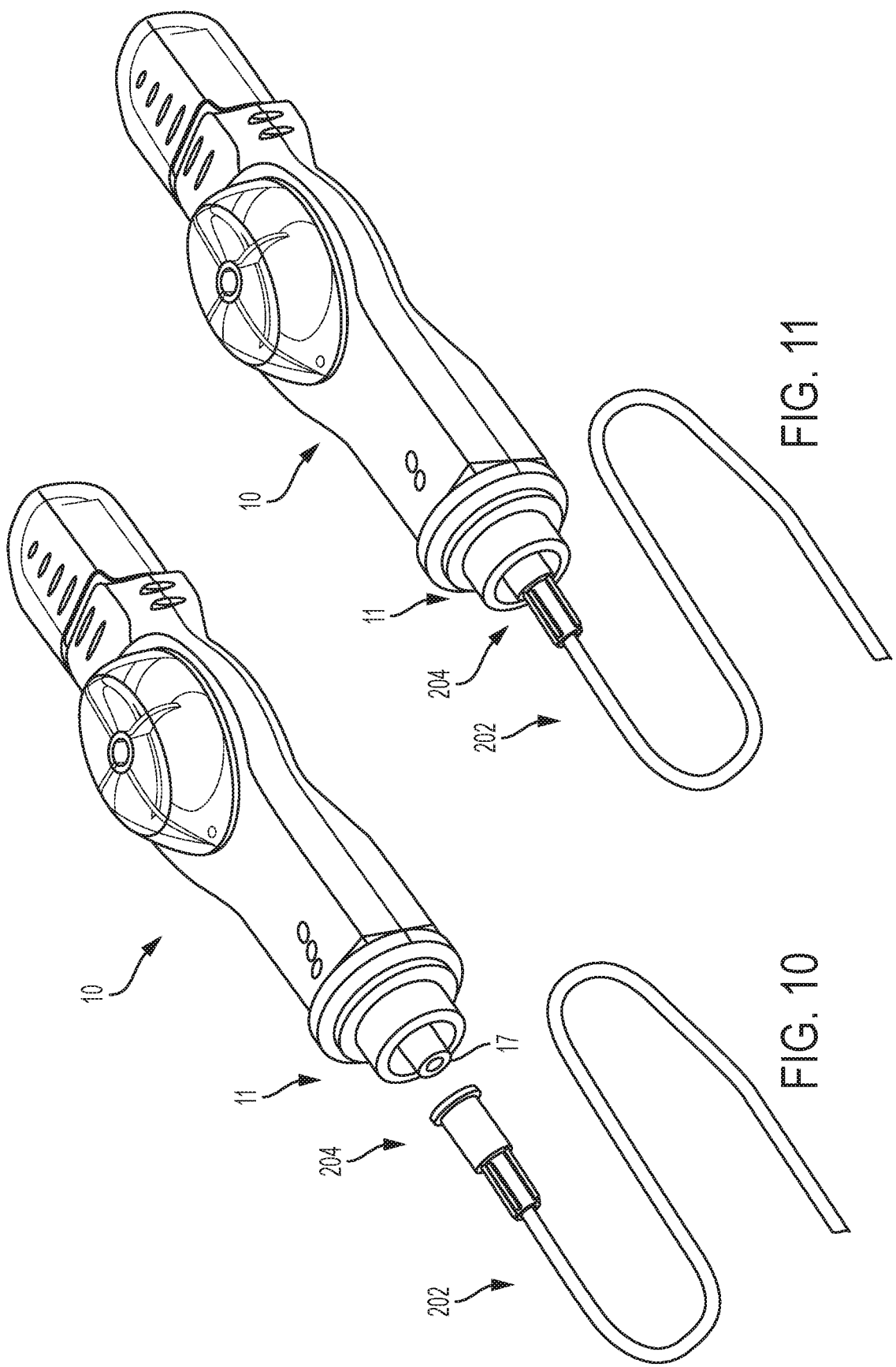

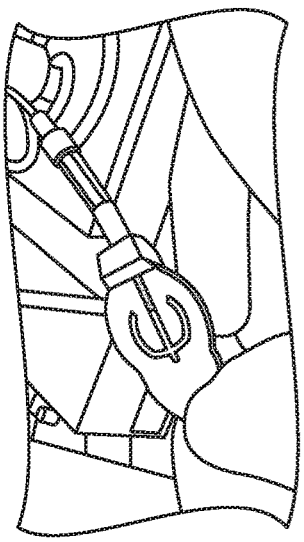

1: CONNECT DEVICE TO BLOOD COLLECTION DEVICE (WINGSET OR LUER). ONCE CONNECTED, PUSH PRIMER BULB TO CREATE VACUUM

FIG. 12

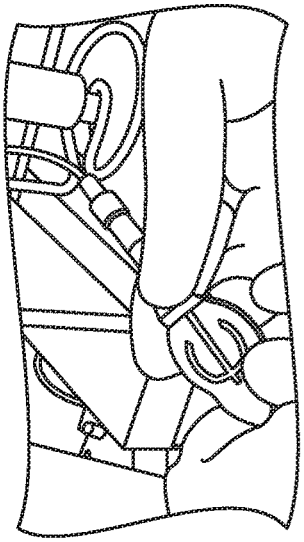

2: VACUUM PULLS SAMPLE INTO DEVICE AIR IN THE LINE ALSO GOES THROUGH THE DEVICE AND THROUGH THE POREX PLUGS.

FIG. 13

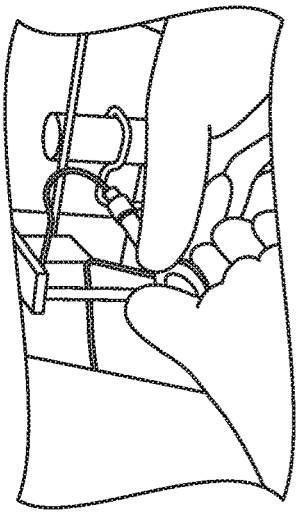

3: VACUUM PULLS SAMPLE & AIR THROUGH DEVICE

FIG. 14

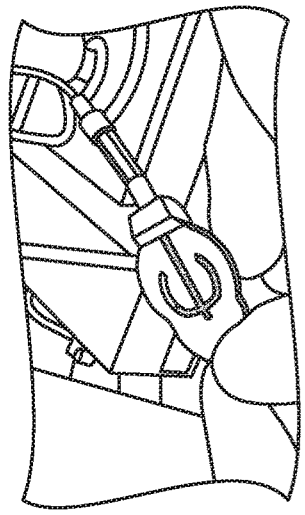

4: AIR CONTINUES TO PASS THROUGH THE POREX PLUGS, AS THE BLOOD FILLS THE DEVICE

FIG. 15

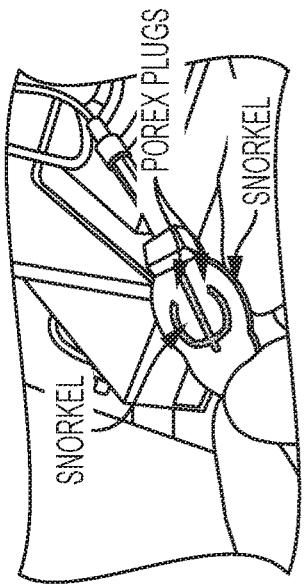

5: BLOOD HAS NOW WETTED OUT THE POREX PLUGS, WHICH SEALS OFF ANY FLUID FROM MOVING THROUGH THE PLUGS.

FIG. 16

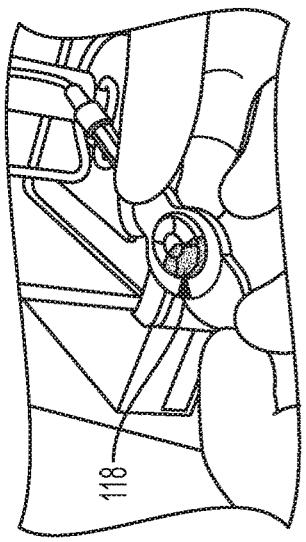

6: THE REMAINING VACUUM IN THE BULB PULLS UP THE FLEXIBLE "PASTRY BAG" ON THE "TOP FILM". AS THE "PASTRY BAG" RISES, IT PULLS BLOOD FROM THE BLOOD COLLECTION DEVICE UNTIL IT IS FILLED.

FIG. 17

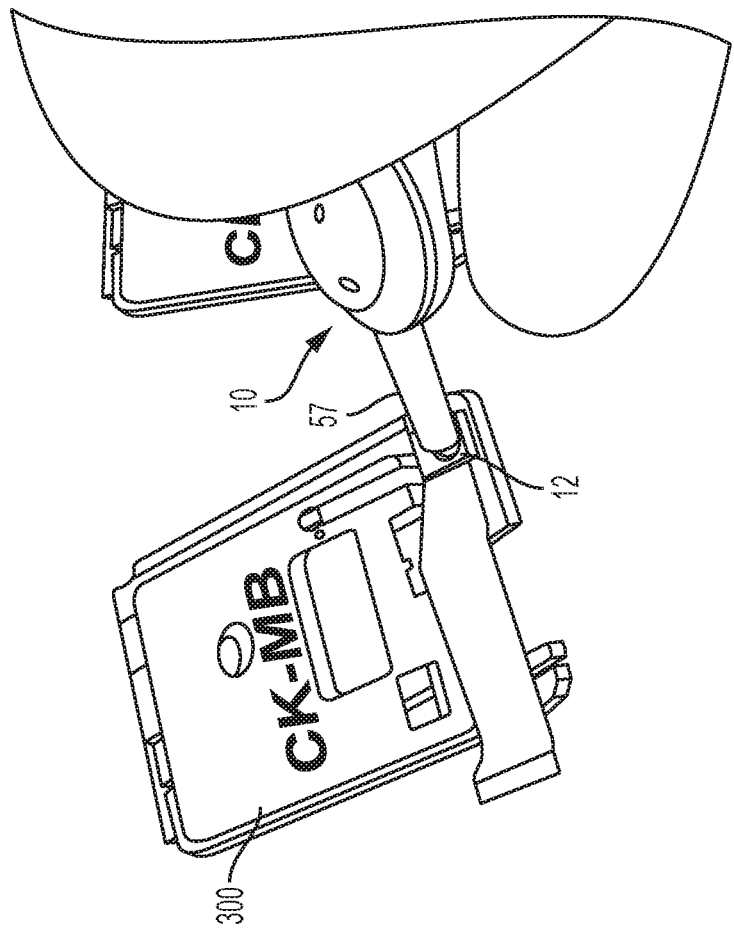
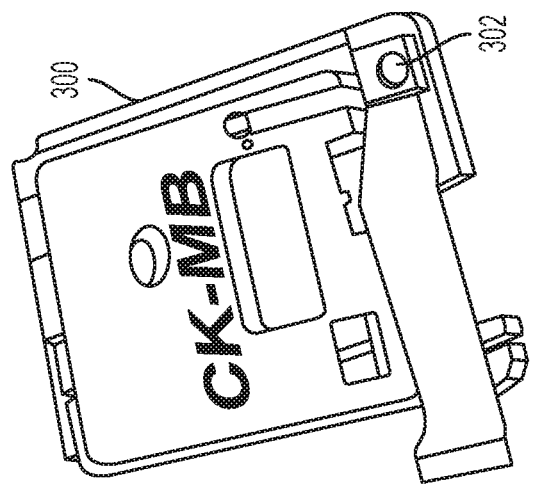
FIG. 24

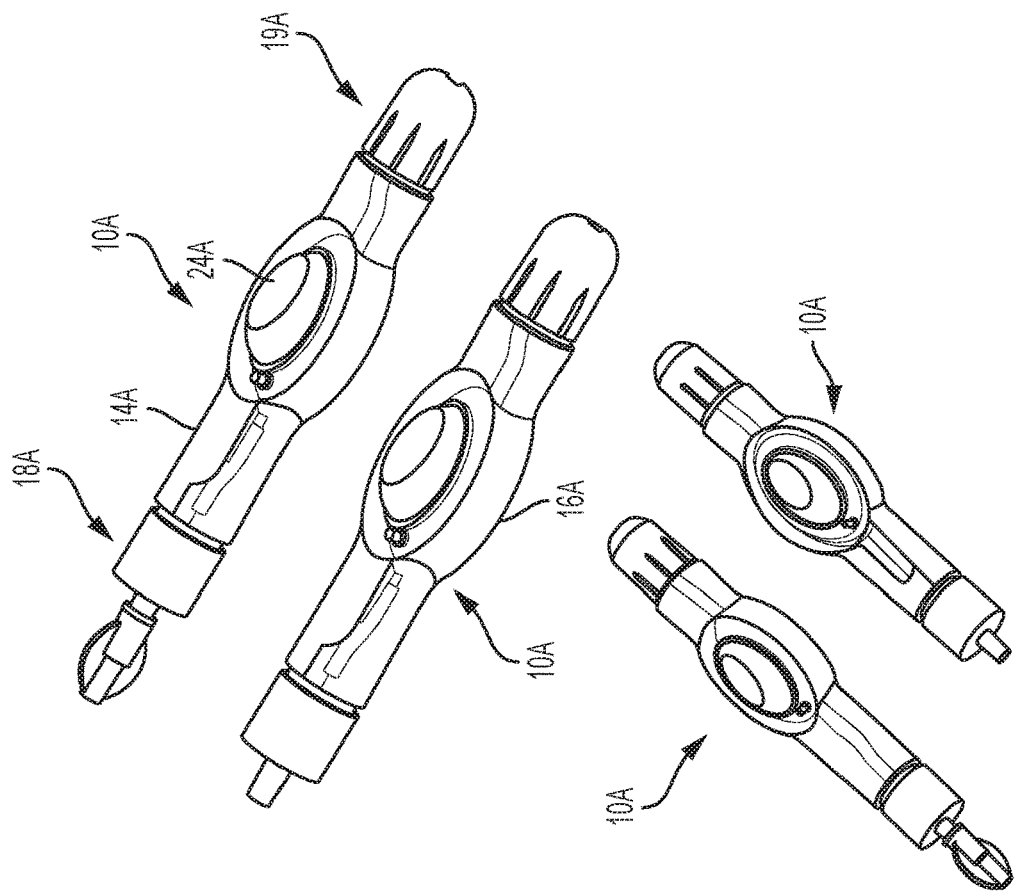
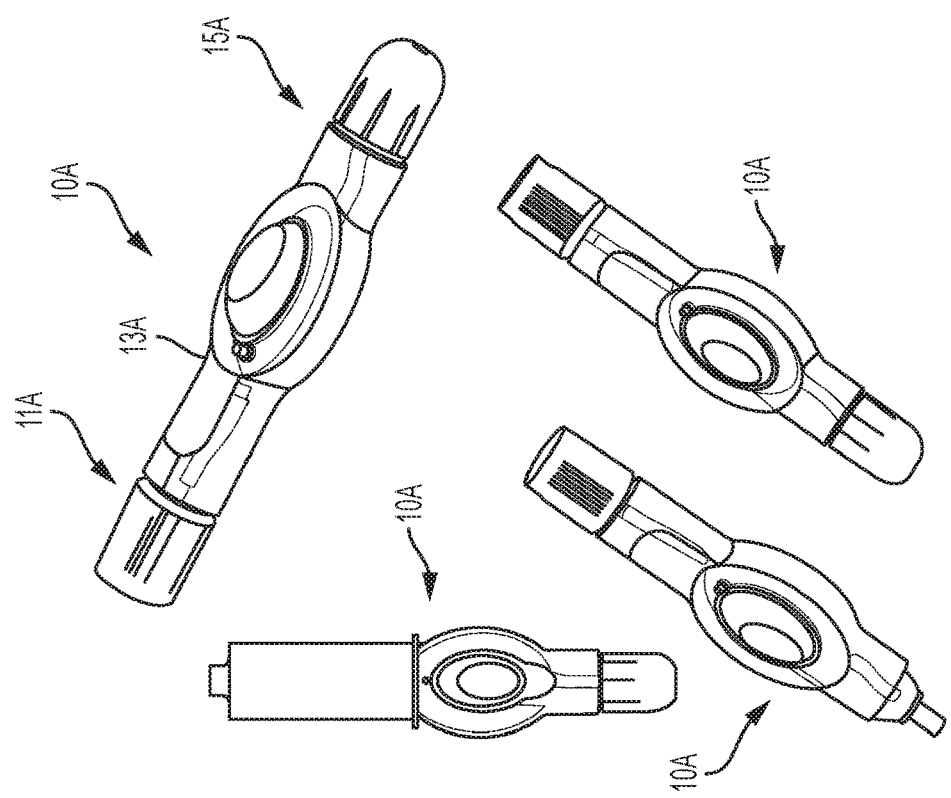
FIG. 27

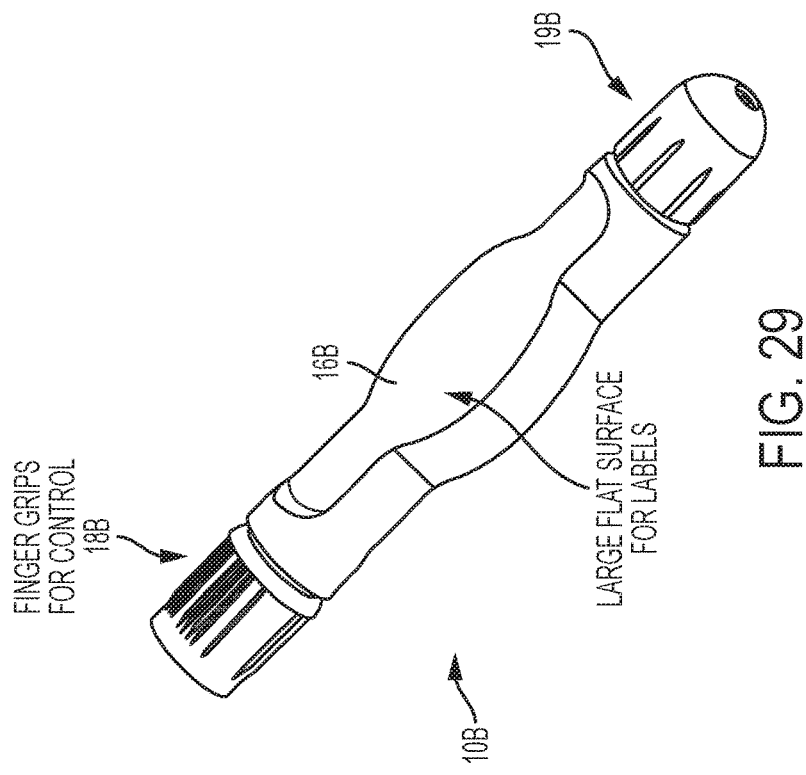
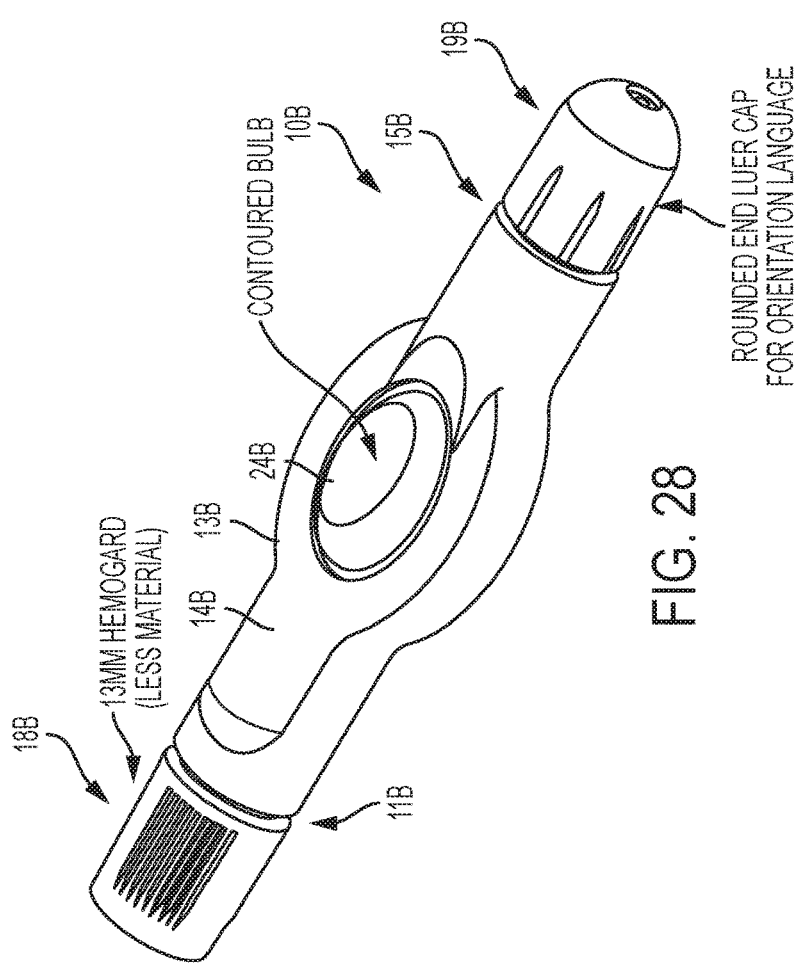

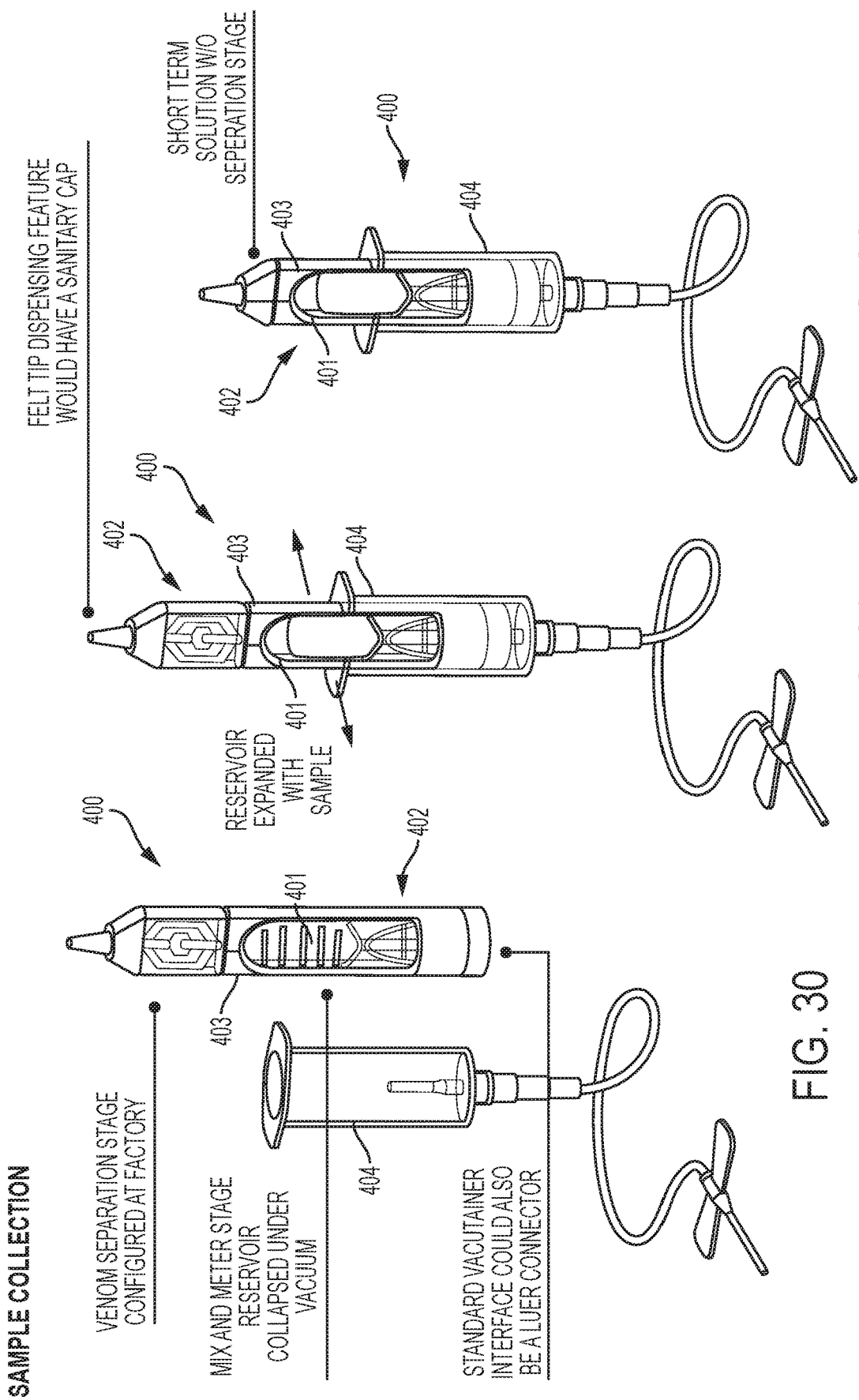

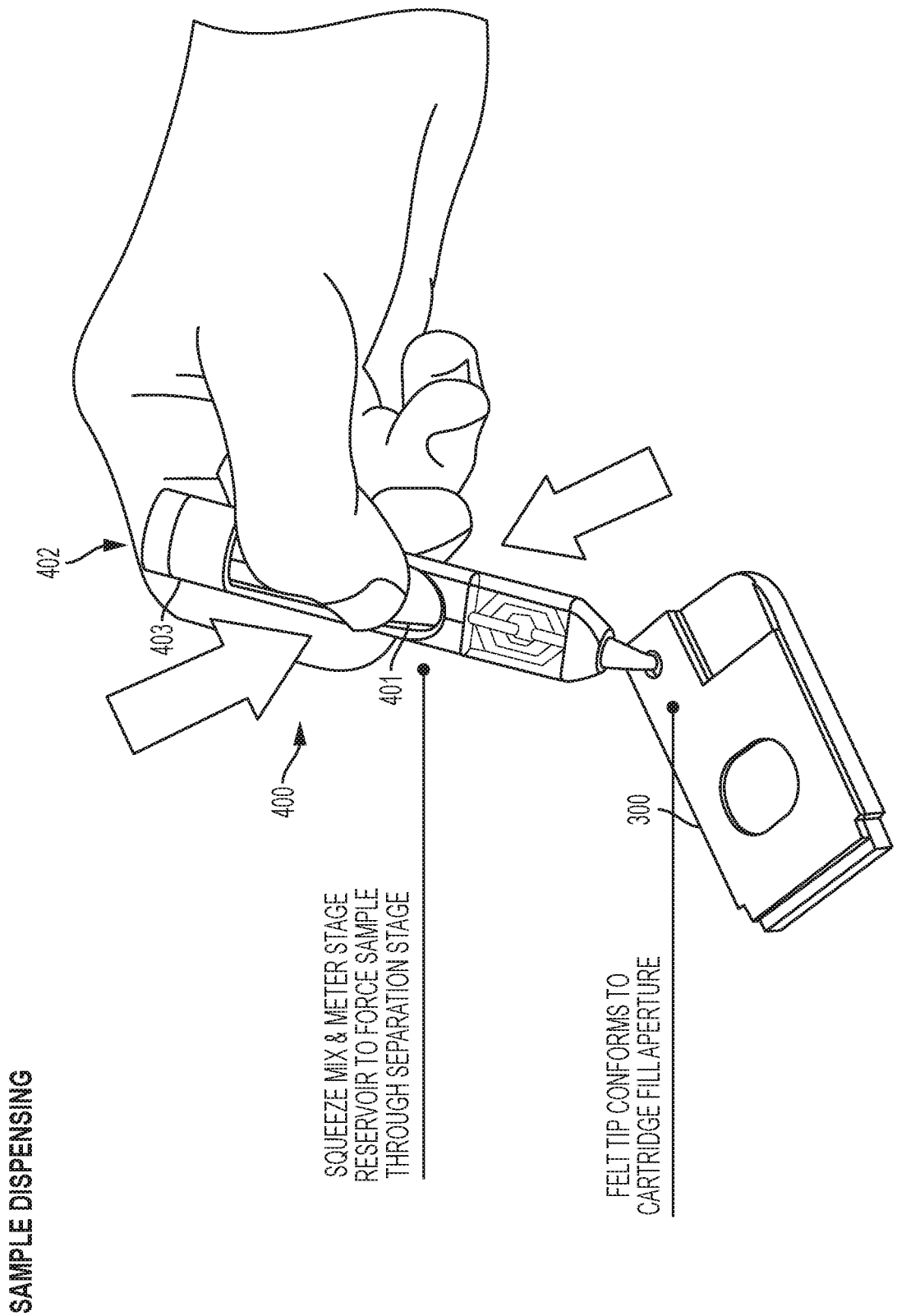

BIOLOGICAL FLUID COLLECTION DEVICE

CROSS-REFERENCE TO RELATED APPLICATIONS

This application claims priority to U.S. Provisional Patent Application Ser. No. 62/181,978, filed Jun. 19, 2015, the entire disclosure of which is hereby expressly incorporated by reference herein.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, and coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process. Furthermore, mixing with an anticoagulant or other component to stabilize the sample must be performed manually.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid collection device that allows a blood sample to be collected anaerobically.

In accordance with an embodiment of the present invention, a biological fluid collection device includes a housing having a superior surface and an inferior surface, wherein a portion of the superior surface defines a cavity having a cavity superior surface; a film engageable with the housing, the film having a film inferior surface and a film superior surface, the film transitionable between an initial position in which the film inferior surface is in contact with the cavity superior surface and a fill position in which the film inferior surface is spaced from the cavity superior surface forming a chamber between the film and the housing; and an actuator disposed at least partially within the housing and in communication with the film and the housing, the actuator transitionable between an original position and a depressed position, wherein after actuation of the actuator to the depressed position, as the actuator returns to the original position, the actuator applies a vacuum to the film superior surface.

In one configuration, the biological fluid collection device includes a second film that seals the inferior surface of the housing. In another configuration, the actuator includes a vent hole. In yet another configuration, the biological fluid collection device is for anaerobic blood collection of a blood sample.

In accordance with another embodiment of the present invention, a biological fluid collection device includes a housing having a superior surface, an inferior surface, an inlet, and an outlet, wherein a portion of the superior surface of the housing defines a cavity having a cavity superior surface, and wherein a portion of the inferior surface of the housing defines a sacrificial flow channel; a venting plug disposed within a portion of the sacrificial flow channel; a film engageable with the housing, the film having a film inferior surface and a film superior surface, the film transitionable between an initial position in which the film inferior surface is in contact with the cavity superior surface and a fill position in which the film inferior surface is spaced from the cavity superior surface forming a chamber between the film and the housing; and an actuator disposed at least partially within the housing and in communication with the film and the housing, the actuator transitionable between an original position and a depressed position, wherein after actuation of the actuator to the depressed position, as the actuator returns to the original position, the actuator simultaneously applies a vacuum to the film superior surface and to the inferior surface of the housing.

In one configuration, the sacrificial flow channel is in fluid communication with the inlet. In another configuration, a portion of the sacrificial flow channel defines a slot. In yet another configuration, the chamber is in fluid communication with the sacrificial flow channel via the slot. In one configuration, the vacuum draws a blood sample into the biological fluid collection device. In another configuration, the chamber is in fluid communication with the outlet. In yet another configuration, the venting plug allows air to pass therethrough and prevents a blood sample from passing therethrough. In one configuration, the biological fluid collection device is for anaerobic blood collection of a blood sample. In another configuration, the biological fluid collection device includes a sample stabilizer disposed between the inlet and the sacrificial flow channel. In yet another configuration, the biological fluid collection device includes a material including pores disposed between the inlet and the sacrificial flow channel; and a dry anticoagulant powder within the pores of the material. In one configuration, a blood sample dissolves and mixes with the dry anticoagulant powder while passing through the material. In another configuration, the material is an open cell foam.

In accordance with another embodiment of the present invention, a biological fluid collection device includes a housing having a superior surface, an inferior surface, a proximal end, a distal end, an inlet channel, and an outlet channel, wherein a portion of the superior surface of the housing defines a cavity having a cavity superior surface, and wherein a portion of the inferior surface of the housing defines a sacrificial flow channel, the sacrificial flow channel comprising: a middle channel having a first middle channel end, a second middle channel end, and defining a slot, the first middle channel end in fluid communication with the inlet channel, the middle channel extending from the first middle channel end to the second middle channel end in a first direction; a first arcuate channel having a first arcuate channel distal end and a first arcuate channel proximal end, the first arcuate channel distal end in communication with the second middle channel end, the first arcuate channel extending from the first arcuate channel distal end to the first arcuate channel proximal end in a second direction; and a second arcuate channel having a second arcuate channel distal end and a second arcuate channel proximal end, the second arcuate channel distal end in communication with the second middle channel end, the second arcuate channel extending from the second arcuate channel distal end to the second arcuate channel proximal end in the second direction; a first venting plug disposed in the first arcuate channel proximal end; and a second venting plug disposed in the second arcuate channel proximal end.

In one configuration, the biological fluid collection device includes a film engageable with the housing, the film having a film inferior surface and a film superior surface, the film transitionable between an initial position in which the film inferior surface is in contact with the cavity superior surface and a fill position in which the film inferior surface is spaced from the cavity superior surface forming a chamber between the film and the housing, wherein the chamber is in fluid communication with the middle channel via the slot. In another configuration, the biological fluid collection device includes an actuator disposed at least partially within the housing and in communication with the film and the housing, the actuator transitionable between an original position and a depressed position, wherein after actuation of the actuator to the depressed position, as the actuator returns to the original position, the actuator simultaneously applies a vacuum to the film superior surface and to the inferior surface of the housing. In yet another configuration, the vacuum draws a blood sample into the biological fluid collection device. In one configuration, the chamber is in fluid communication with the outlet channel. In another configuration, the second direction is substantially opposite the first direction. In yet another configuration, the first arcuate channel extends in the second direction away from the second middle channel end towards the first middle channel end. In one configuration, the second arcuate channel extends in the second direction away from the second middle channel end towards the first middle channel end. In another configuration, the first arcuate channel and the second arcuate channel are on opposing sides of the middle channel. In yet another configuration, the first venting plug allows air to pass therethrough and prevents a blood sample from passing therethrough. In one configuration, the second venting plug allows air to pass therethrough and prevents a blood sample from passing therethrough. In another configuration, the biological fluid collection device is for anaerobic blood collection of a blood sample.

In accordance with another embodiment of the present invention, a biological fluid collection device includes a housing having a proximal end, a distal end, a superior surface and an inferior surface, wherein a portion of the superior surface defines a cavity having a cavity superior surface, the proximal end connectable to a first blood collection device; a film engageable with the housing, the film having a film inferior surface and a film superior surface, the film transitionable between an initial position in which the film inferior surface is in contact with the cavity superior surface and a fill position in which the film inferior surface is spaced from the cavity superior surface forming a chamber between the film and the housing; an actuator disposed at least partially within the housing and in communication with the film and the housing, the actuator transitionable between an original position and a depressed position, wherein after actuation of the actuator to the depressed position, as the actuator returns to the original position, the actuator applies a vacuum to the film superior surface; and a first interface removably connectable to the proximal end of the housing, the first interface connectable to a second blood collection device.

In one configuration, the biological fluid collection device is for anaerobic blood collection of a blood sample.

In accordance with another embodiment of the present invention, a biological fluid collection device includes a housing having a proximal end, a distal end, a superior surface and an inferior surface, wherein a portion of the superior surface defines a cavity having a cavity superior surface, the distal end comprising a plurality of slots; a film engageable with the housing, the film having a film inferior surface and a film superior surface, the film transitionable between an initial position in which the film inferior surface is in contact with the cavity superior surface and a fill position in which the film inferior surface is spaced from the cavity superior surface forming a chamber between the film and the housing; and an actuator disposed at least partially within the housing and in communication with the film and the housing, the actuator transitionable between an original position and a depressed position, wherein after actuation of the actuator to the depressed position, as the actuator returns to the original position, the actuator applies a vacuum to the film superior surface.

In one configuration, the biological fluid collection device is for anaerobic blood collection of a blood sample.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 7A is an exploded view of an interface for a biological fluid collection device in accordance with an embodiment of the present invention.

FIG. 7B is an exploded, perspective view of a superior surface of a biological fluid collection device in accordance with an embodiment of the present invention.

FIG. 7C is a perspective view of a biological fluid collection device in accordance with an embodiment of the present invention.

FIG. 8 is an exploded view of a biological fluid collection device and a first blood collection device in accordance with an embodiment of the present invention, with an interface connected to the biological fluid collection device.

FIG. 9 is a perspective view of a biological fluid collection device connected to a first blood collection device in accordance with an embodiment of the present invention, with an interface connected to the biological fluid collection device.

FIG. 10 is an exploded view of a biological fluid collection device and a second blood collection device in accordance with an embodiment of the present invention.

FIG. 11 is a perspective view of a biological fluid collection device connected to a second blood collection device in accordance with an embodiment of the present invention.

FIG. 12 is a perspective view of a first step of using a device of the present disclosure in accordance with an embodiment of the present invention.

FIG. 13 is a perspective view of a second step of using a device of the present disclosure in accordance with an embodiment of the present invention.

FIG. 14 is a perspective view of a third step of using a device of the present disclosure in accordance with an embodiment of the present invention.

FIG. 15 is a perspective view of a fourth step of using a device of the present disclosure in accordance with an embodiment of the present invention.

FIG. 16 is a perspective view of a fifth step of using a device of the present disclosure in accordance with an embodiment of the present invention.

FIG. 17 is a perspective view of a sixth step of using a device of the present disclosure in accordance with an embodiment of the present invention.

FIG. 24 is a perspective view of a seventh step of using a device of the present disclosure in accordance with an embodiment of the present invention.

FIG. 27 is perspective views of a biological fluid collection device in accordance with other embodiments of the present invention.

FIG. 28 is a perspective view of a superior surface of a biological fluid collection device in accordance with another embodiment of the present invention.

FIG. 29 is a perspective view of an inferior surface of a biological fluid collection device in accordance with another embodiment of the present invention.

FIG. 30 is an exploded view of a biological fluid collection device and a first blood collection device in accordance with another embodiment of the present invention.

FIG. 31 is a perspective view of a biological fluid collection device connected to a first blood collection device in accordance with another embodiment of the present invention.

FIG. 32 is a perspective view of a biological fluid collection device connected to a first blood collection device in accordance with another, embodiment of the present invention.

FIG. 33 is a perspective view of a biological fluid collection device and a point-of-care testing device in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
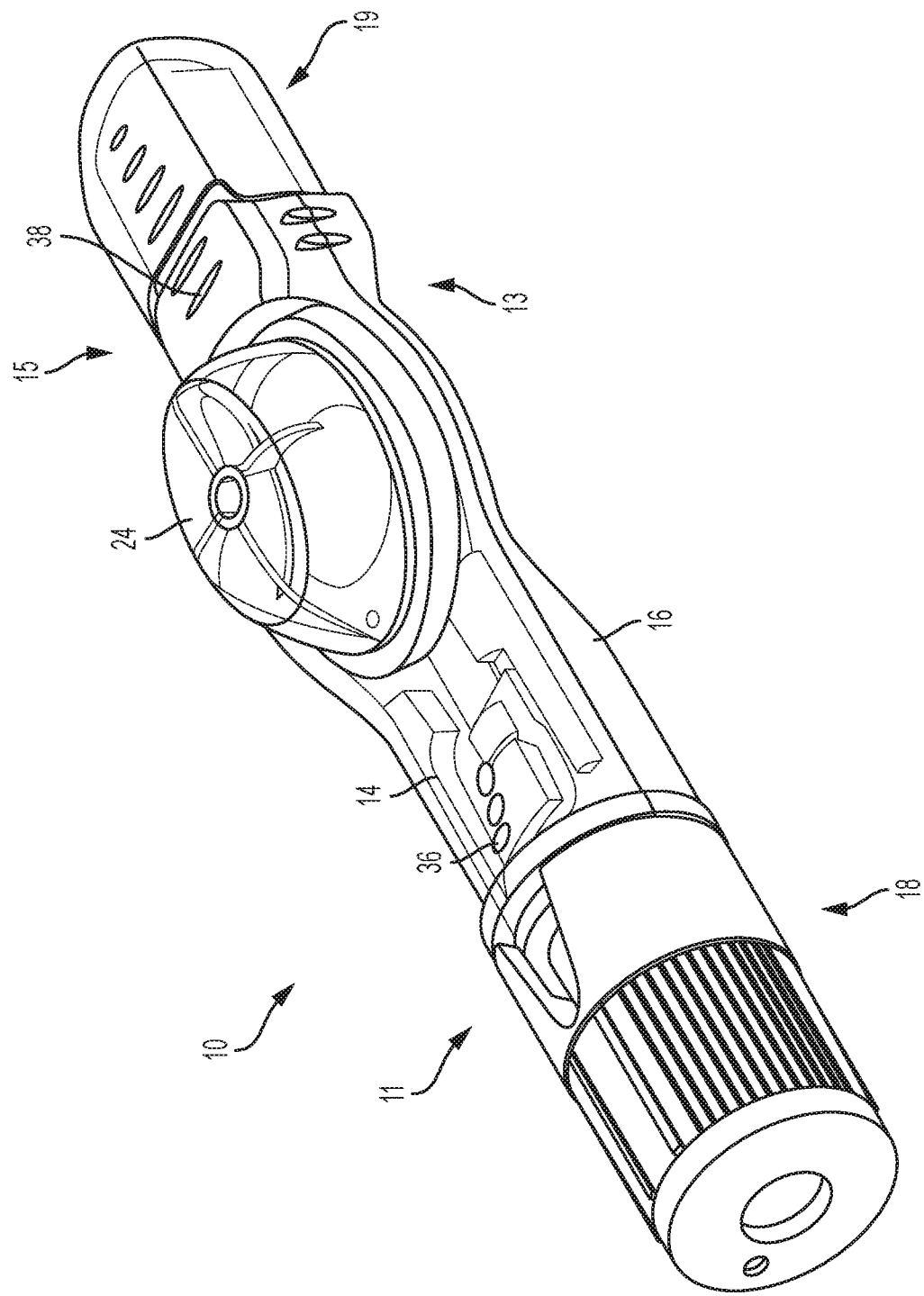
FIG. 1 is a perspective view of a biological fluid collection device in accordance with an embodiment of the present invention.
Figure 2:
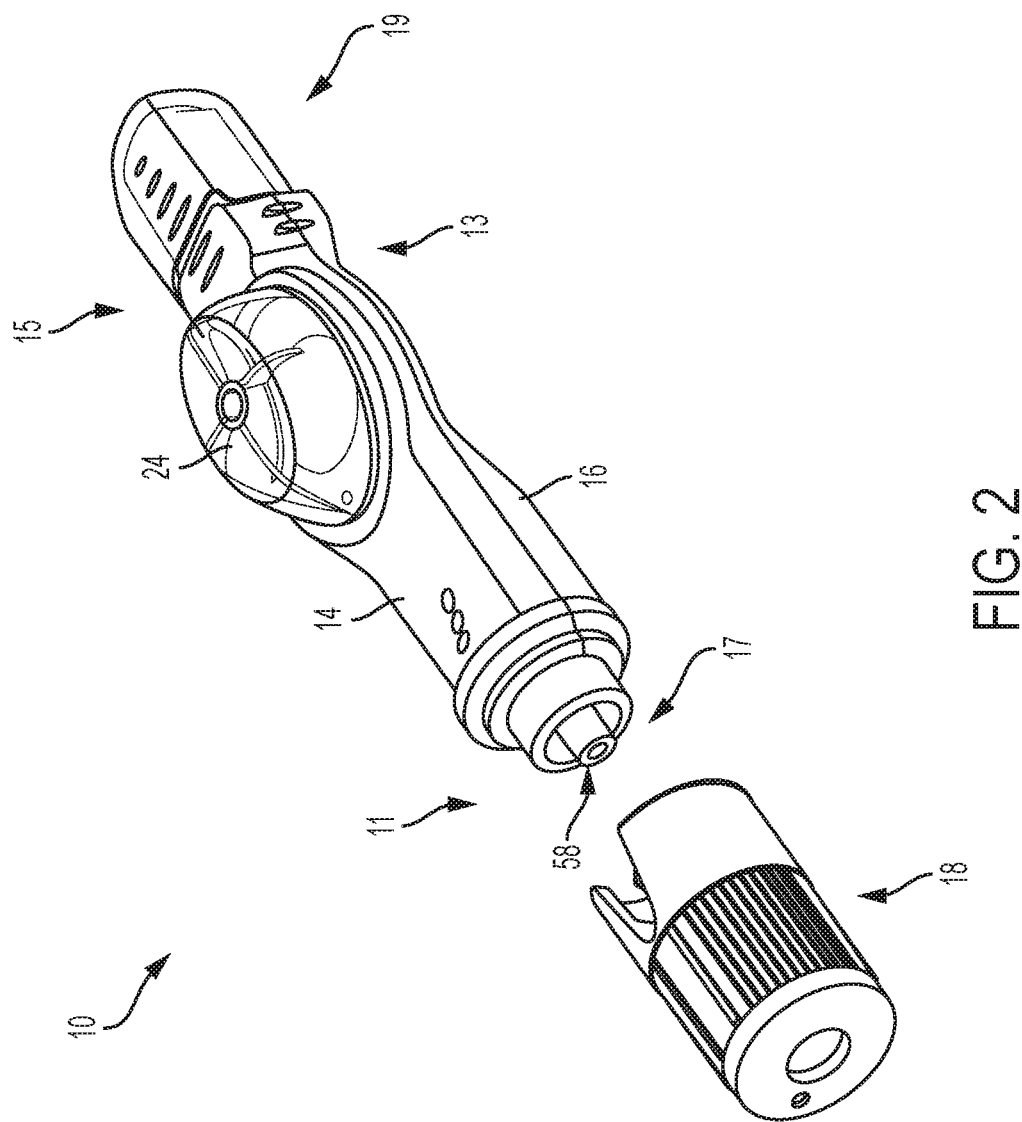
FIG. 2 is an exploded, perspective view of a superior surface of a biological fluid collection device in accordance with an embodiment of the present invention.
Figure 3:
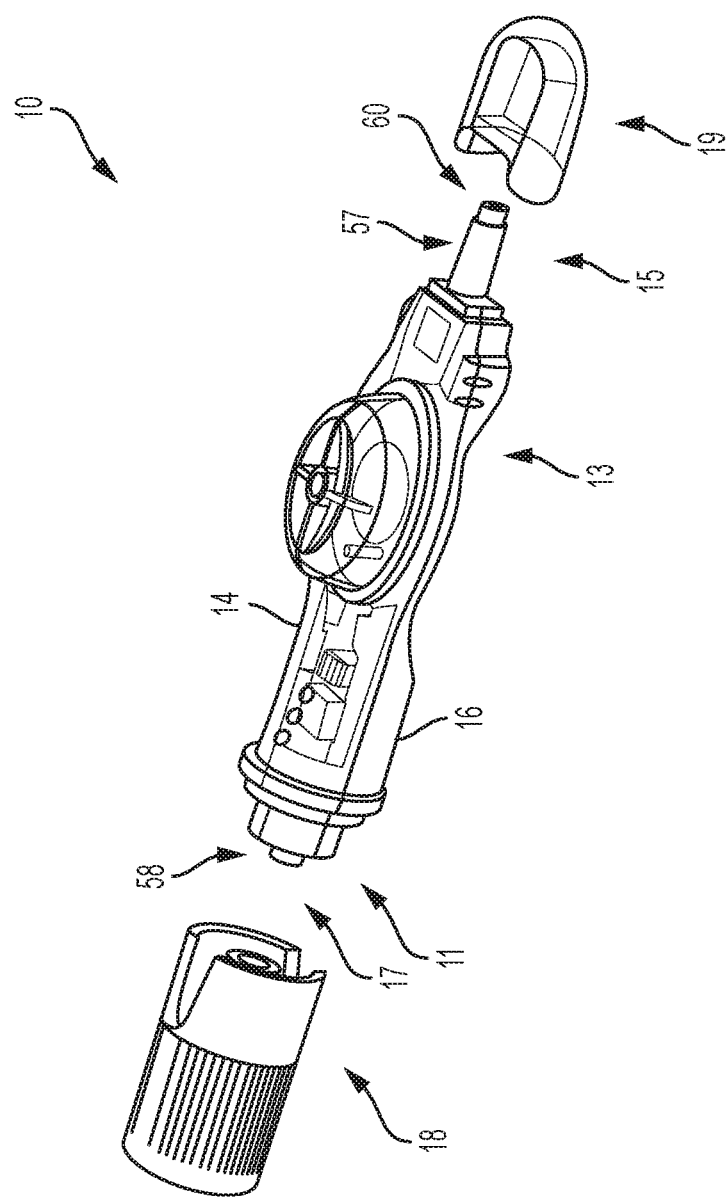
FIG. 3 is an exploded, perspective view of a superior surface of a biological fluid collection device in accordance with an embodiment of the present invention.
Figure 4:
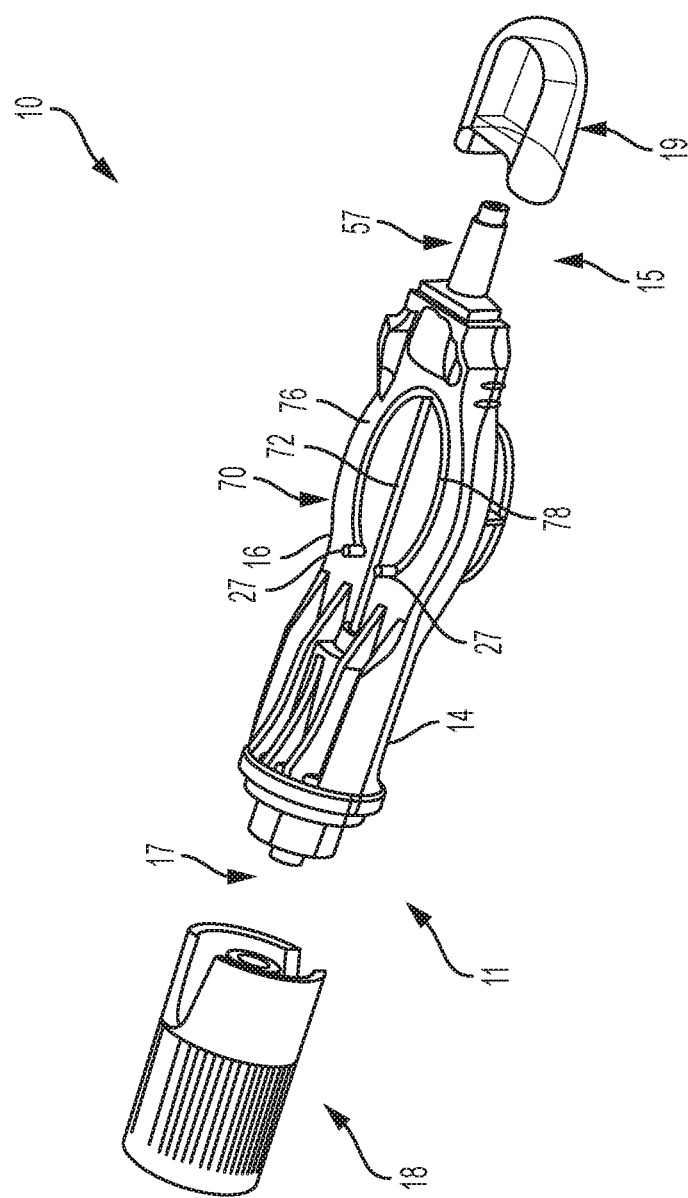
FIG. 4 is an exploded, perspective view of an inferior surface of a biological fluid collection device in accordance with an embodiment of the present invention.
Figure 5:
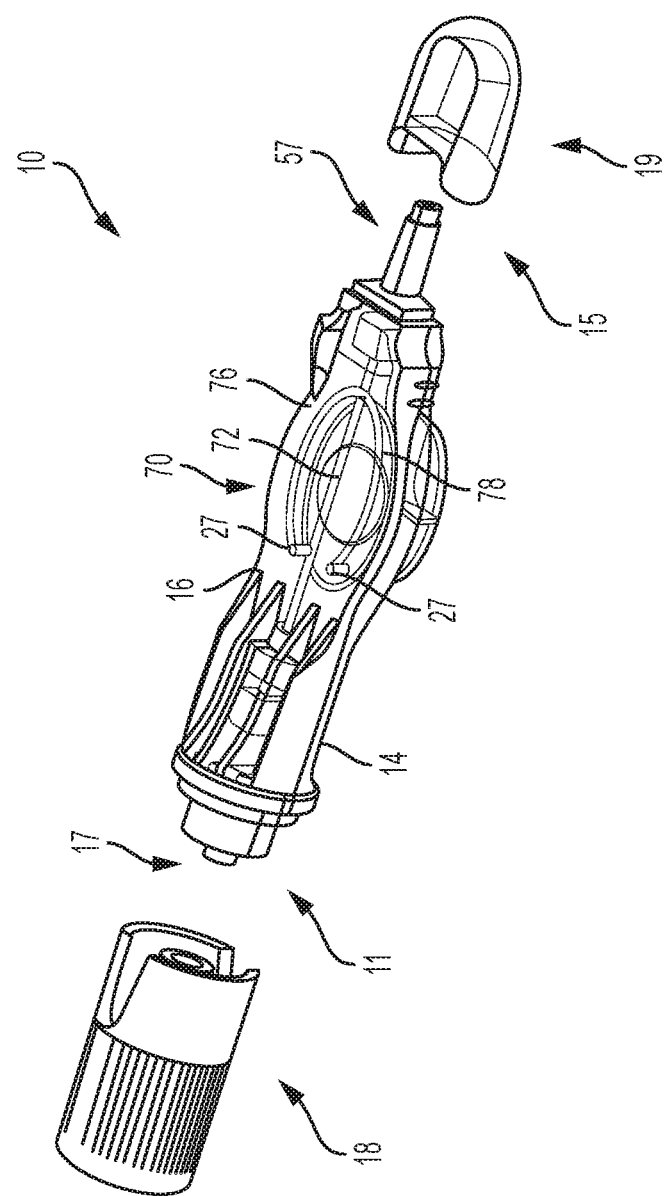
FIG. 5 is an exploded, perspective view of an inferior surface of a biological fluid collection device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge leading to a repeat of the sample collection and testing process, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; 5) collecting a sample anaerobically; and 6) stabilizing the sample at the point of collection.

FIGS. 1-6 illustrate an exemplary embodiment of a biological fluid collection device of the present disclosure. Referring to FIGS. 1-6 and 20-23, a biological fluid collection device 10 is shown that allows a blood sample 12 to be collected anaerobically. The biological fluid collection device 10 includes a housing 13 having a superior surface 14 and an inferior surface 16, a proximal end 11, a distal end 15, a first interface 18, and a cap 19. In one embodiment, a male luer fitting 17 is disposed at the proximal end 11 of the biological fluid collection device 10. The first interface 18 is removably connectable to the proximal end 11 of the housing 13. The cap 19 is removably connectable to the distal end 15 of the housing 13 and shields and protects a dispensing tip 57.

Figure 6:
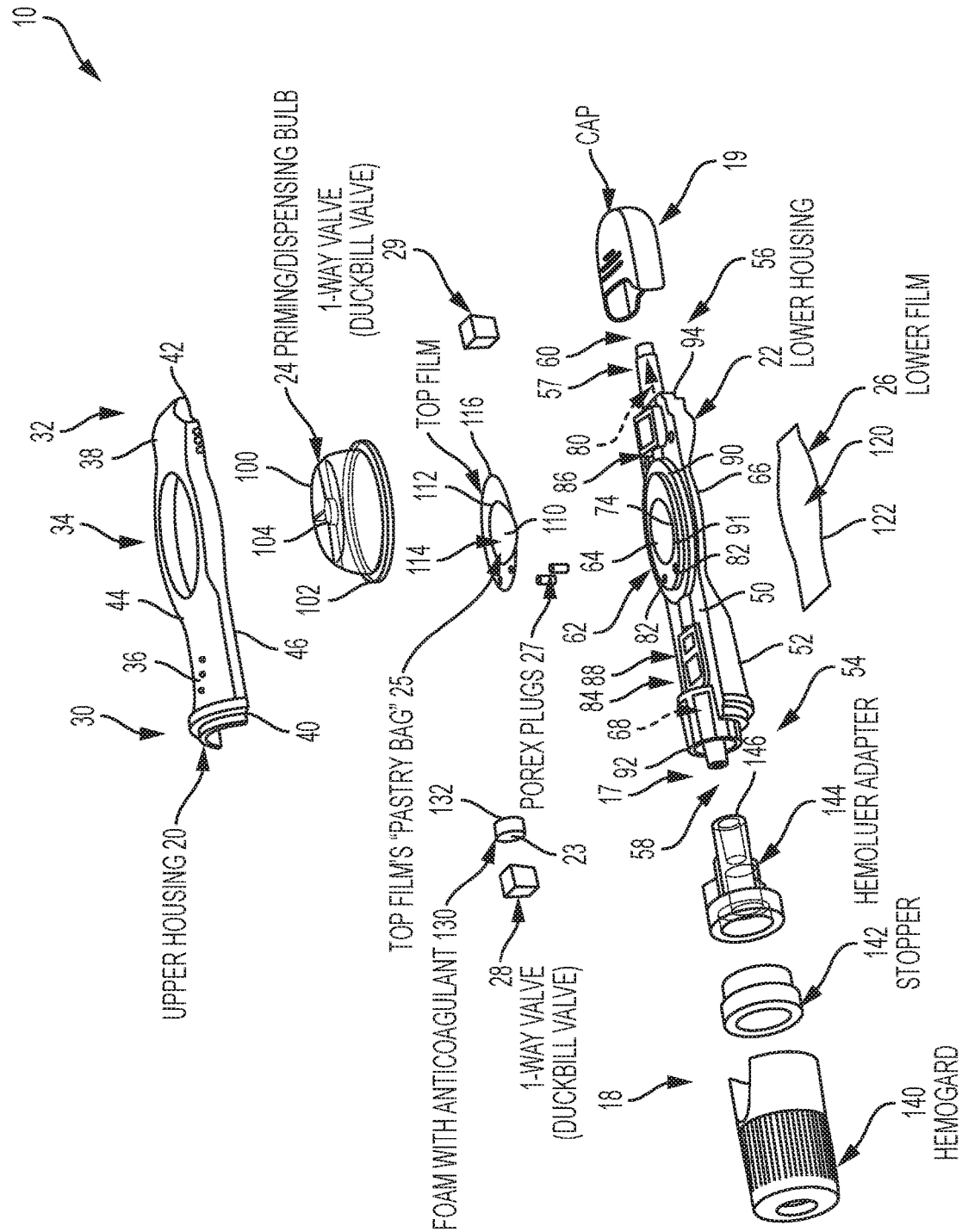
FIG. 6 is an exploded view of a biological fluid collection device in accordance with an embodiment of the present invention.

Referring to FIG. 6, the biological fluid collection device 10 includes an upper housing 20, a lower housing 22, an actuator 24, an upper film or pastry bag 25, a lower film 26, plugs 27, a first valve 28, a second valve 29, and an anticoagulant 23. In one embodiment, the biological fluid collection device 10 may include one plug 27. In other embodiments, the biological fluid collection device 10 may include more than one plug 27.

The upper housing 20 includes a proximal end 30, a distal end 32, an actuator receiving cavity 34, a first finger grip portion 36, a second finger grip portion 38, a first connection portion 40, a second connection portion 42, a superior surface 44, and an inferior surface 46.

The lower housing 22 includes a superior surface 50, an inferior surface 52, a proximal end 54, a distal end 56, a dispensing tip 57, an inlet 58, an outlet 60, a cavity 62 having a cavity superior surface 64 and a cavity inferior surface 66, an inlet flow channel 68, a sacrificial flow channel 70 (FIGS. 4-5) having a middle channel 72 (FIGS. 4-5) including a slot 74, a first arcuate channel 76 (FIGS. 4-5), and a second arcuate channel 78 (FIGS. 4-5), an outlet flow channel 80, a plug receiving aperture 82, a first valve receiving aperture 84, a second valve receiving aperture 86, an anticoagulant receiving aperture 88, an actuator receiving portion 90, an upper film receiving portion 91, a third connection portion 92, and a fourth connection portion 94.

In one embodiment, a portion of the superior surface 50 of the lower housing 22 defines a cavity 62 having a cavity superior surface 64. In one embodiment, a portion of the inferior surface 52 of the lower housing 22 defines a sacrificial flow channel 70. In one embodiment, the sacrificial flow channel 70 is in fluid communication with the inlet 58. In one embodiment, a chamber 118 of the upper film 25 is in fluid communication with the sacrificial flow channel 70 via the slot 74. In one embodiment, the chamber 118 of the upper film 25 is in fluid communication with the outlet 60.

In one embodiment, the sacrificial flow channel 70 includes a middle channel 72 having a first middle channel end, a second middle channel end, and defining a slot 74. In one embodiment, the first middle channel end is in fluid communication with the inlet channel 68. In one embodiment, the middle channel 72 extends from the first middle channel end to the second middle channel end in a first direction.

In one embodiment, the sacrificial flow channel 70 includes a first arcuate channel 76 having a first arcuate channel distal end and a first arcuate channel proximal end. In one embodiment, the first arcuate channel distal end is in communication with the second middle channel end. In one embodiment, the first arcuate channel 76 extends from the first arcuate channel distal end to the first arcuate channel proximal end in a second direction.

In one embodiment, the sacrificial flow channel 70 includes a second arcuate channel 78 having a second arcuate channel distal end and a second arcuate channel proximal end. In one embodiment, the second arcuate channel distal end is in communication with the second middle channel end. In one embodiment, the second arcuate channel 78 extends from the second arcuate channel distal end to the second arcuate channel proximal end in the second direction.

In one embodiment, the second direction is substantially opposite the first direction. In one embodiment, the first arcuate channel 76 extends in the second direction away from the second middle channel end towards the first middle channel end. In one embodiment, the second arcuate channel 78 extends in the second direction away from the second middle channel end towards the first middle channel end. In one embodiment, the first arcuate channel 76 and the second arcuate channel 78 are on opposing sides of the middle channel 72.

The upper housing 20 is connectable with the lower housing 22. In one embodiment, the upper housing 20 is connectable with the lower housing 22 via engagement of the first connection portion 40 of the upper housing 20 with the third connection portion 92 of the lower housing 22 and the second connection portion 42 of the upper housing 20 with the fourth connection portion 94 of the lower housing 22. The connection portions 40, 42, 92, 94 of the upper and lower housing 20, 22 may include any type of connection mechanism to secure the upper and lower housing 20, 22 theretogether. For example, the connection portions 40, 42, 92, 94 of the upper and lower housing 20, 22 may include a threaded portion, snap fit mechanism, a ball detent, locking tabs, spring loaded locking mechanism, latch, adhesive, or other similar connection mechanism.

The actuator 24 includes a button portion 100 and a flange portion 102. In one embodiment, the actuator 24 may include a vent hole 104. In one embodiment, the actuator may be any mechanism that creates a vacuum. In one embodiment, the vacuum created by the actuator 24 draws a blood sample into the biological fluid collection device 10.

In one embodiment, the actuator 24 is disposed at least partially within the housing 13 and is in communication with the upper film 25 and a portion of the housing 13, and the actuator 24 is transitionable between an original position and a depressed position. In one embodiment, after actuation of the actuator 24 to the depressed position, as the actuator 24 returns to the original position, the actuator 24 applies a vacuum to the upper film superior surface 112. In one embodiment, after actuation of the actuator 24 to the depressed position, as the actuator 24 returns to the original position, the actuator 24 simultaneously applies a vacuum to the upper film superior surface 112 and to the inferior surface 52 of the lower housing 22.

In one embodiment, the actuator 24 comprises a priming and dispensing bulb. In one embodiment, the flange portion 102 of the actuator 24 allows the actuator 24 to be securely positioned with the actuator receiving portion 90 of the lower housing 22. In one embodiment, the button portion 100 of the actuator 24 extends through the actuator receiving cavity 34 of the upper housing 20. The button portion 100 of the actuator 24 is able to be depressed as described in more detail below. Referring to FIGS. 30-33, in some embodiments, an actuator 401 of a biological fluid collection device 400 does not extend beyond an exterior wall 403 of the biological fluid collection device 400 as discussed below. The actuator 24 allows a blood sample to be collected within the biological fluid collection device 10 and dispensed from the biological fluid collection device 10 as described in more detail below.

The upper film 25 includes an inferior surface 110, a superior surface 112, a dome portion 114, and a flange portion 116. The upper film 25 forms a chamber 118 (FIGS. 17 and 23) as described in more detail below. The upper film 25 is transitionable between an initial position in which the inferior surface 110 of the upper film 25 is in contact with the superior surface 64 of the cavity 62 and a fill position in which the film inferior surface 110 is spaced from the cavity superior surface 64 thereby forming a chamber 118 between the upper film 25 and a portion of the lower housing 22. In one embodiment, the flange portion 116 of the upper film 25 allows the upper film 25 to be securely positioned with the upper film receiving portion 91 of the lower housing 22 within the biological fluid collection device 10. In one embodiment, the upper film 25 is a thin, flexible film that allows for a preevacuated blood collection chamber.

In the initial position, the inferior surface 110 of the upper film 25 is in face-to-face contact with the superior surface 64 of the cavity 62 of the lower housing 22. For example, the hemispherical cavity of the upper film 25 matches the shape of the hemispherical cavity in the lower housing 22. With the upper film's flat surface sealed to the cavity 62 of the lower housing 22, there is minimal gap/air between the inferior surface 110 of the upper film's hemispherical geometry and the lower housing's hemispherical cavity 62. As the biological fluid collection device 10 fills with blood, the upper film 25 swells and fills with blood as described in more detail below. When the biological fluid collection device 10 is filled, the majority of the device's blood sample is stored anaerobically in the chamber 118 of the upper film 25 as described in more detail below.

The lower film 26 includes a superior surface 120 and an inferior surface 122. The lower film 26 seals the inferior surface 52 of the lower housing 22.

The biological fluid collection device 10 may contain a sample stabilizer or an anticoagulant 23. For example, the anticoagulant may be added to a blood sample 12 as the blood sample 12 flows within the biological fluid collection device 10. The anticoagulant 23 may be contained in-line or as a coating layer above, within, or on top of a flow channel of the biological fluid collection device, or any combination thereof. In one embodiment, the sample stabilizer is disposed between the inlet 58 and the sacrificial flow channel 70.

In one embodiment, the anticoagulant 23 is securely positioned within the anticoagulant receiving aperture 88 of the lower housing 22 within the inlet flow channel 68 of the biological fluid collection device 10.

In one embodiment, the biological fluid collection device 10 may include a material 130 having pores 132 that may include the anticoagulant 23. In one embodiment, the material 130 is a sponge material. In one embodiment, the material 130 is an open cell foam. In one embodiment, the open cell foam is treated with an anticoagulant to form a dry anticoagulant powder finely distributed throughout the pores 132 of the material 130. As a blood sample 12 flows through the material 130 within the biological fluid collection device 10, the blood sample 12 is exposed to the anticoagulant powder throughout the internal micro pore structure of the material 130. In one embodiment, the material 130 including pores 132 is disposed between the inlet 58 and the sacrificial flow channel 70. In one embodiment, a blood sample dissolves and mixes with the dry anticoagulant powder while passing through the material 130.

In one embodiment, the material 130 is a soft deformable open cell foam that is inert to blood. In one embodiment, the open cell foam is a Basotect® foam available from BASF. Such a foam is a Melamine foam which is an open cell foam material consisting of a formaldehyde-melamine-sodium bisulfate copolymer. The Melamine foam is a flexible, hydrophilic open cell foam that is resistant to heat and many organic solvents.

A method of loading an anticoagulant to a material 130 having pores 132 will now be discussed. In one embodiment, the method includes soaking the material 130 in a liquid solution of the anticoagulant and water; evaporating the water of the liquid solution; and forming a dry anticoagulant powder within the pores 132 of the material 130.

The method of the present disclosure enables precisely controlled loading of an anticoagulant into the material 130 by soaking it with an anticoagulant and water solution and then drying the material 130 to form a finely distributed dry anticoagulant powder throughout the pores 132 of the material 130.

Anticoagulants such as Heperin or EDTA (Ethylene Diamine Tetra Acetic Acid) as well as other blood stabilization agents could be introduced into, the material 130 as a liquid solution by soaking the material 130 in the liquid solution of a desired concentration. After evaporating the liquid phase, e.g., evaporating the water from a water and Heperin solution, a dry anticoagulant powder is formed finely distributed throughout the internal structure of the material 130. For example, the dry anticoagulant powder is formed finely distributed throughout the pores 132 of the material 130. In a similar manner, the material 130 could be treated to provide a hydrophobic, hydrophilic, or reactive internal pore surface.

In other embodiments, the biological fluid collection device 10 may be adapted to contain other sample stabilizers to provide passive and fast mixing of a blood sample 12 with a sample stabilizer. The sample stabilizer, can be an anticoagulant, or a substance designed to preserve a specific element within the blood such as, for example, RNA, protein analyte, or other element. In one embodiment, the sample stabilizer is heparin or EDTA. In one embodiment, a plurality of biological fluid collection devices 10 could include different sample stabilizers. A biological fluid collection device 10 of the present disclosure provides flexibility in the nature of the additives and/or sample stabilizers introduced for a blood sample.

In one embodiment, the plugs 27 may be formed of a material having pores. The pores allow air to evacuate the biological fluid collection device 10 as described in more detail below. In one embodiment, the plugs 27 may be a Porex® material available from Porex Corporation.

In one embodiment, the plugs 27 are securely positioned, respectively, within the plug receiving apertures 82 of the lower housing 22 within a portion of the flow channels of the biological fluid collection device 10. In one embodiment, the plugs 27 are disposed within a portion of the sacrificial flow channel 70.

In one embodiment, the plugs 27 are venting plugs that allow air to pass therethrough and prevent a blood sample from passing therethrough. In one embodiment, the venting plug is a porous plug. In one embodiment, the venting plug includes a carboxymethylcellulose additive.

Carboxymethylcellulose is a "self-sealing" additive that swells when it comes into contact with a liquid. When this additive is placed within a porous material, particularly a hydrophobic material, it allows air to vent prior to swelling shut when liquid reaches the carboxymethylcellulose. This prevents liquid from escaping a collection chamber of the biological fluid collection device.

In one embodiment, a first venting plug 27 is disposed in the first arcuate channel 76 proximal end and a second venting plug 27 is disposed in the second arcuate channel 78 proximal end.

Referring to FIGS. 6-7C, the first interface 18 includes a cap or Hemogard 140, a stopper 142, and an adapter 144 having a female luer fitting 146. The first interface 18 allows for the biological fluid collection device 10 to have multiple connection types to a variety of different blood collection devices.

The first interface 18 allows a biological fluid collection device 10 of the present disclosure to have the capability to either connect to a blood collection device with a holder 200 (FIGS. 8 and 9) or a standard Luer 204 (FIGS. 10 and 11). If the first interface 18 is left attached, a user may connect via a holder 200 (FIGS. 8 and 9). If the first interface 18 is removed, the male Luer fitting 17 at the proximal end 11 of the biological fluid collection device 10 can be used to connect the biological fluid collection device 10 to a second blood collection device 202 via a standard Luer interface 204 as shown in FIG. 11. An advantage of the first interface 18 and the biological fluid collection device 10 of the present disclosure is that it enables a single SKU device to accommodate a variety of connection options.

Referring to FIGS. 1-24 and 34-38, use of a biological fluid collection device 10 of the present disclosure will now be described.

Referring to FIGS. 8-11, a user can select one of the ways, sources, or methods that the biological fluid collection device 10 is able to receive a blood sample. For example, the system of the present disclosure allows the biological fluid collection device 10 to receive a blood sample from a variety of sources including, but not limited to, a holder or a first blood collection device 200 (FIGS. 8 and 9), a second blood collection device 202 via a standard Luer interface 204 (FIGS. 10 and 11), a wingset blood collection device, or other blood collection device.

If it is desired to use a holder 200, the first interface 18 is connected to the proximal end 11 as shown in FIGS. 7C, 8, and 9. With the first interface 18 connected to the proximal end 11, the biological fluid collection device 10 can be connected to a holder 200 via a standard Hemogard/holder interface as shown in FIG. 9.

If it is desired to use a second blood collection device 202, the first interface 18 is removed from the proximal end 11 of the biological fluid collection device 10 as shown in FIG. 10. In this manner, the male Luer fitting 17 at the proximal end 11 of the biological fluid collection device 10 can be used to connect the biological fluid collection device 10 to a second blood collection device 202 via a standard Luer interface 204 as shown in FIG. 11.

Figure 18:
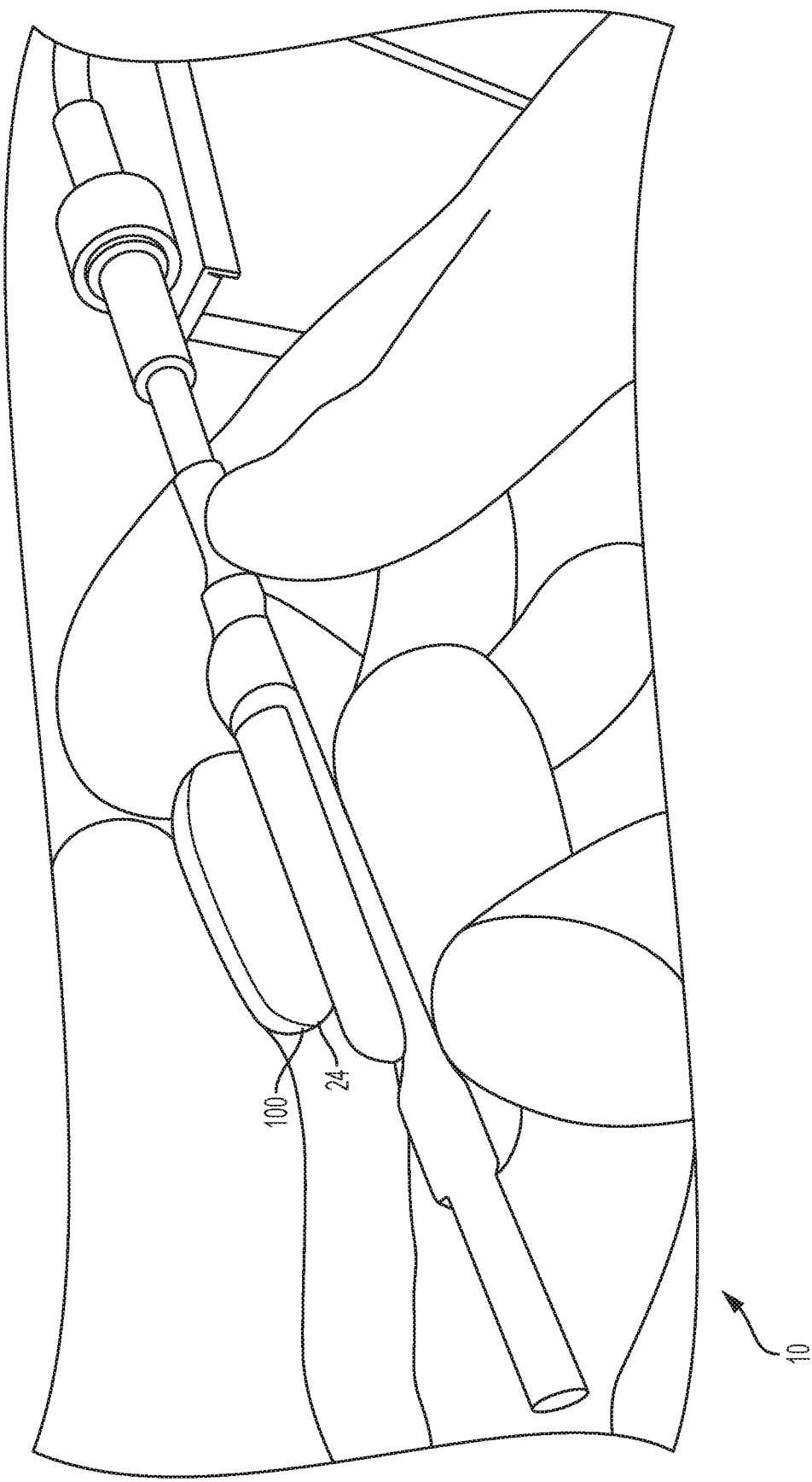
FIG. 18 is a perspective view of a first step of using a device of the present disclosure in accordance with an embodiment of the present invention.
Figure 19:
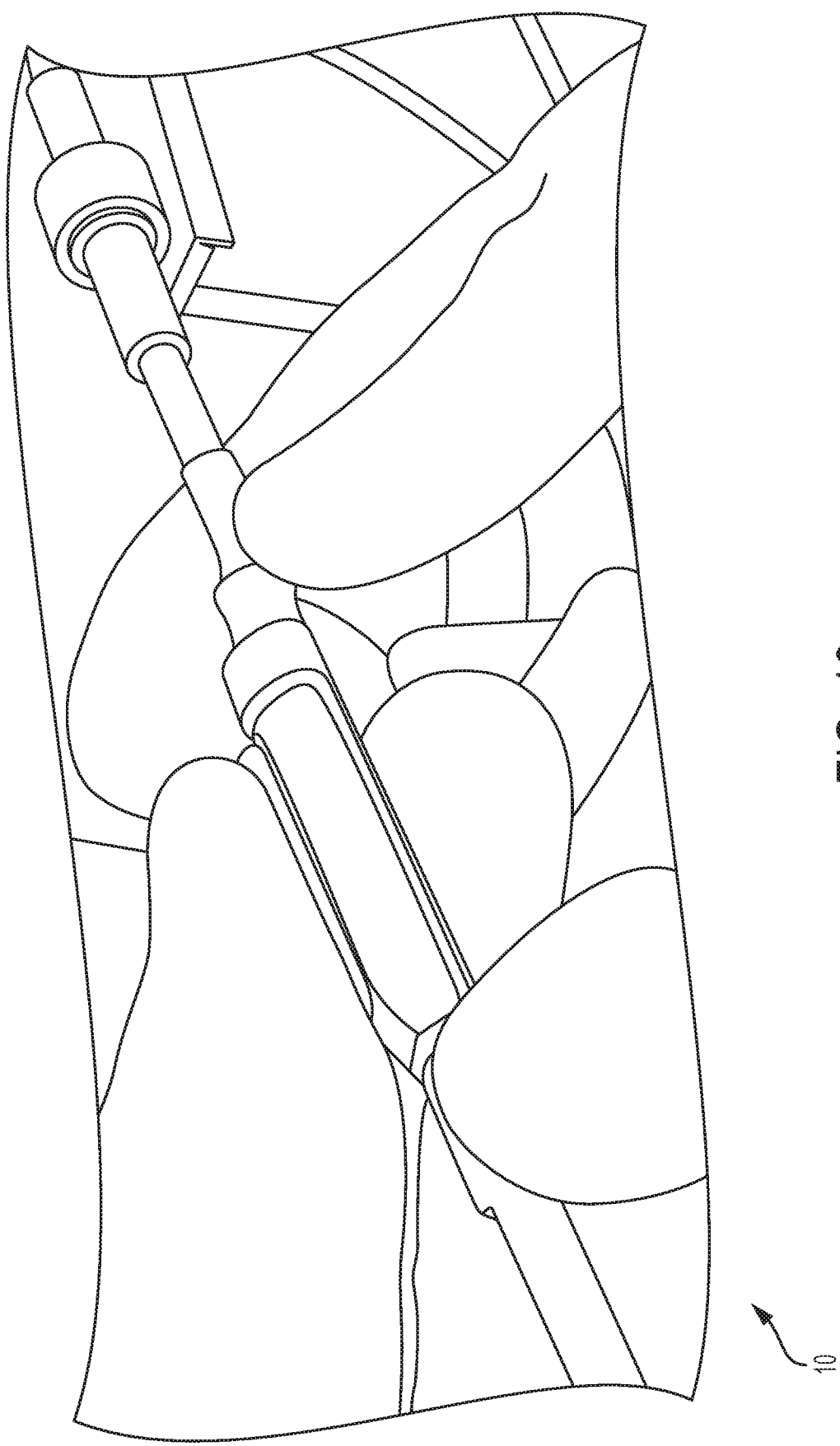
FIG. 19 is a perspective view of a second step of using a device of the present disclosure in accordance with an embodiment of the present invention.
Figure 20:
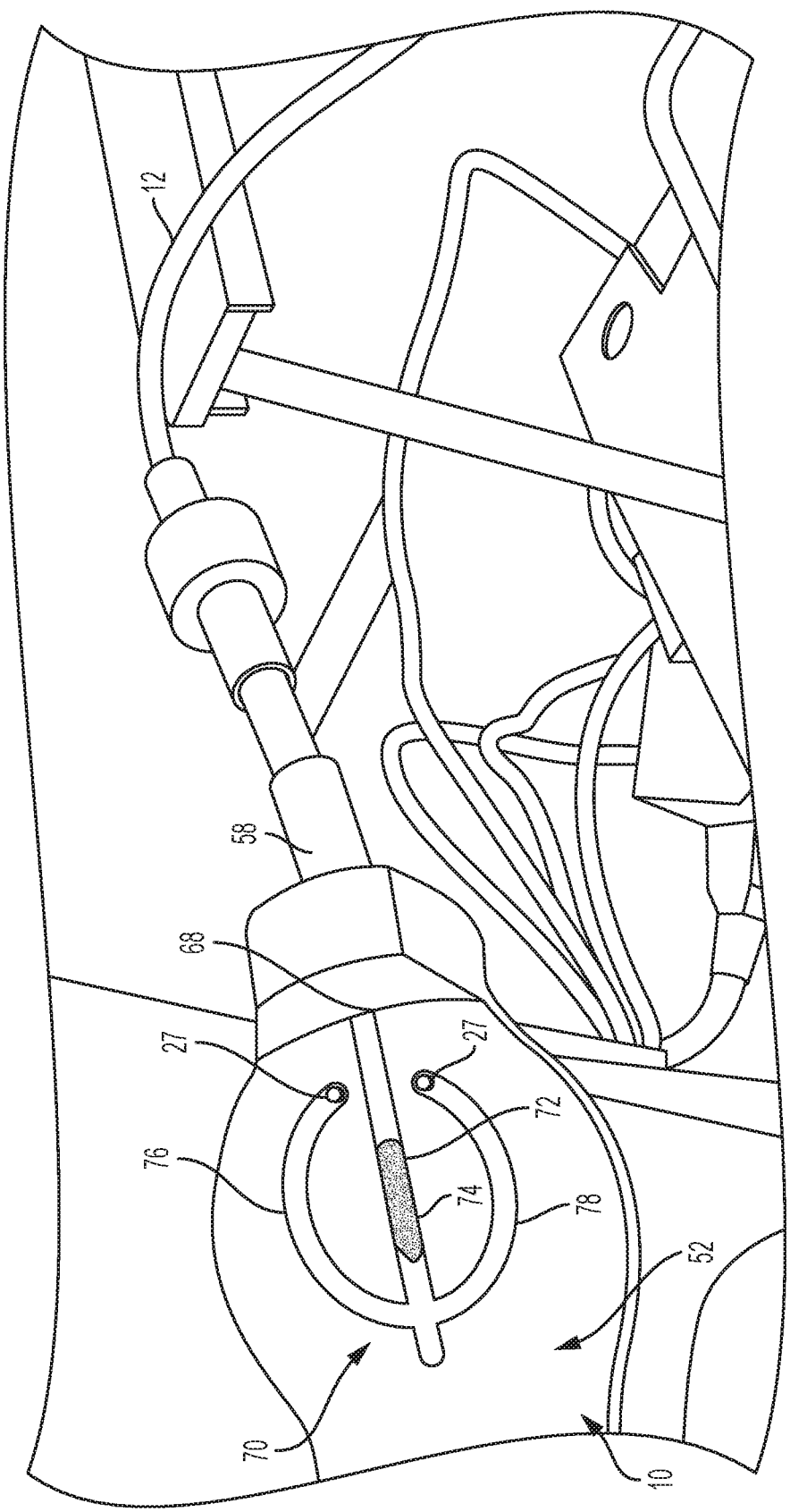
FIG. 20 is a perspective view of a third step of using a device of the present disclosure in accordance with an embodiment of the present invention.
Figure 21:
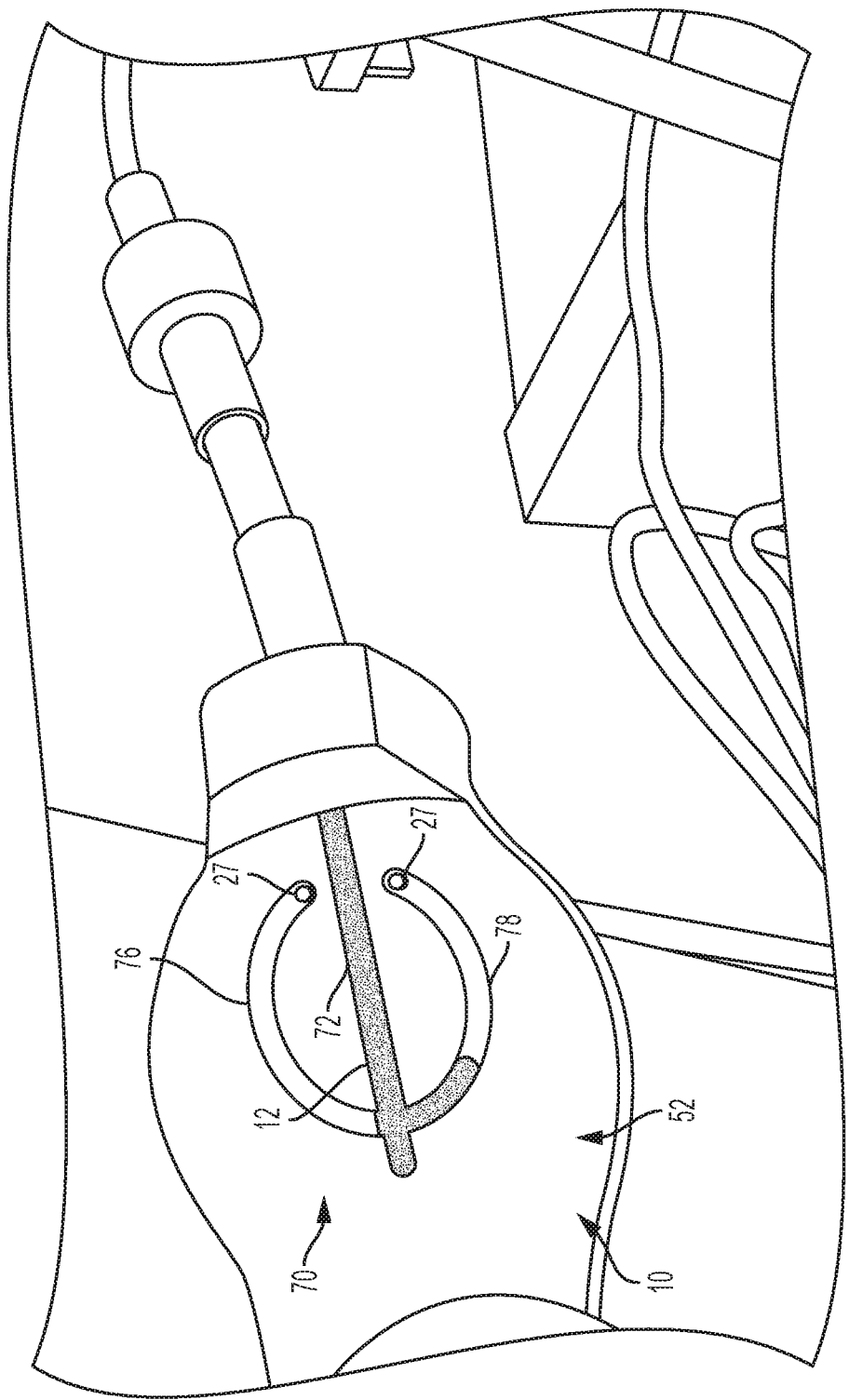
FIG. 21 is a perspective view of a fourth step of using a device of the present disclosure in accordance with an embodiment of the present invention.
Figure 22:
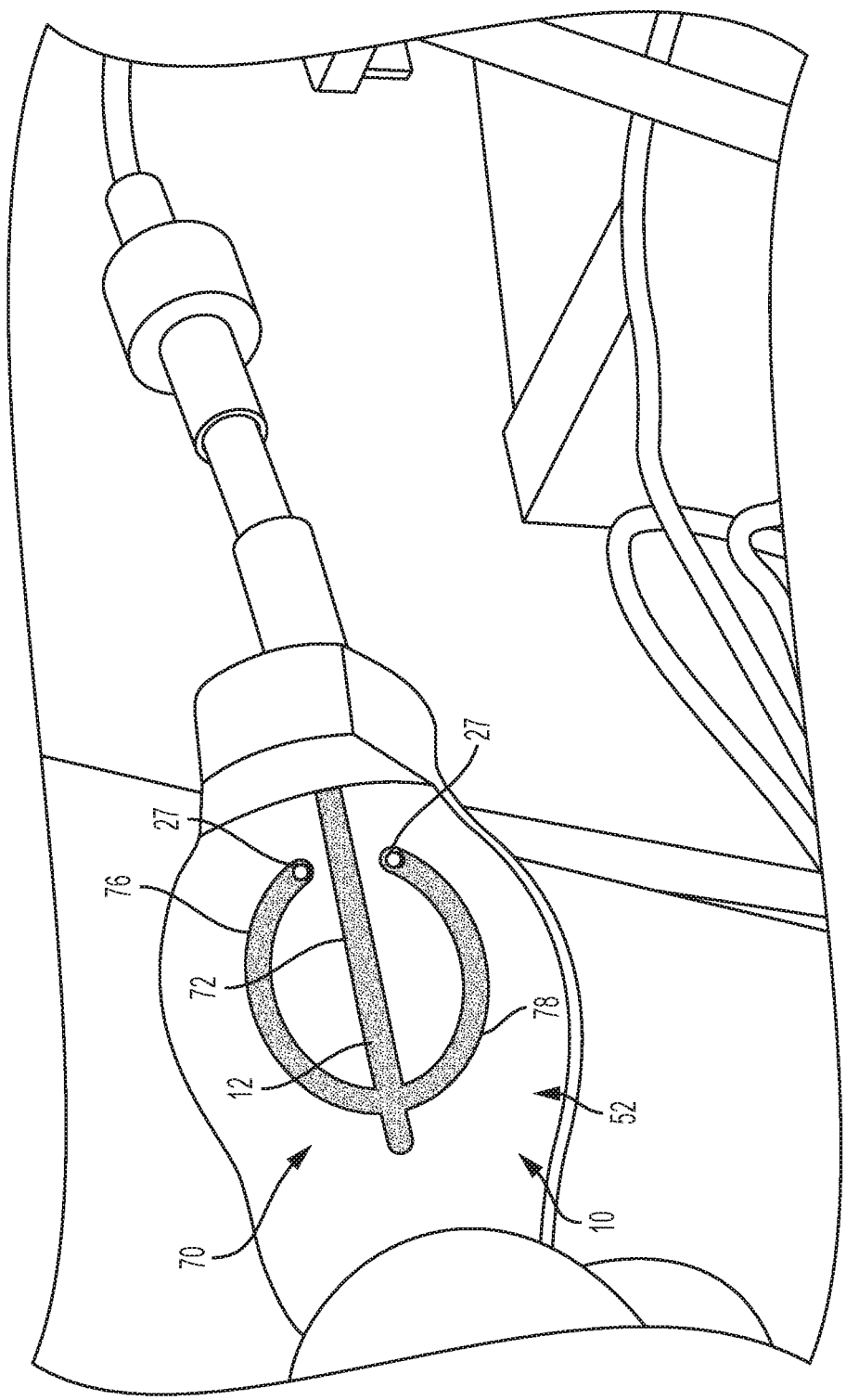
FIG. 22 is a perspective view of a fifth step of using a device of the present disclosure in accordance with an embodiment of the present invention.

Once a desired method or source is selected for collecting a blood sample into the biological fluid collection device 10, the button portion 100 of the actuator 24 is depressed as shown in FIGS. 18 and 19. Upon release of the button portion 100 of the actuator 24, as the button portion 100 of the actuator 24 returns to its original position, the actuator 24 creates and applies a vacuum simultaneously to the superior surface 112 of the upper film 25 and to the inferior surface 52 of the lower housing 22, e.g., through the plugs 27 and the sacrificial flow channel 70. This vacuum created pulls a blood sample 12 into the proximal end 11 of the biological fluid collection device 10 as shown in FIGS. 13, 14, 20, and 21. The biological fluid collection device 10 also vents air as it fills with a blood sample 12. For example, the design of the biological fluid collection device 10 is such that the resistance going through the plugs 27 is less than, i.e., takes less energy than, it would take for the upper film 25 to rise. In this manner, air passes through and out the biological fluid collection device 10 via the plugs 27 as the blood sample 12 begins to fill the middle channel 72 of the sacrificial flow channel 70 as shown in FIGS. 14 and 21. The biological fluid collection device 10 allows for evacuation of air underneath the upper film 25, e.g., via the sacrificial flow channel 70 and plugs 27 of the inferior surface 52 of the lower housing 22. Referring to FIGS. 14, 15, and 21, air continues to pass through the plugs 27 and out of the biological fluid collection device 10 as the blood sample 12 continues to fill the arcuate channels 76, 78 of the biological fluid collection device 10. Referring to FIGS. 16 and 22, once the blood sample 12 fills the sacrificial flow channel 70, e.g., the middle channel 72, the first arcuate channel 76, and the second arcuate channel 78, the blood sample 12 then wets out the plugs 27, which seals off any fluid from moving through the plugs 27. By venting any air within the biological fluid collection device 10 through the plugs 27 and the sacrificial flow channel 70, all the possible air throughout the system is evacuated before the chamber 118 of the upper film 25 fills with blood or as the chamber 118 fills with blood.

Referring to FIGS. 14-16 and 20-22, the pathway of the sacrificial flow channel 70 is designed such that the air and blood initially collected flow in a first direction via the middle channel 72 and then back in an opposite second direction via the arcuate channels 76, 78. This increases the time before the blood contacts and wets the plugs 27 thereby ensuring that any air within the biological fluid collection device 10 is expelled. Thus, all air within the biological fluid collection device 10 is evacuated.

Figure 23:
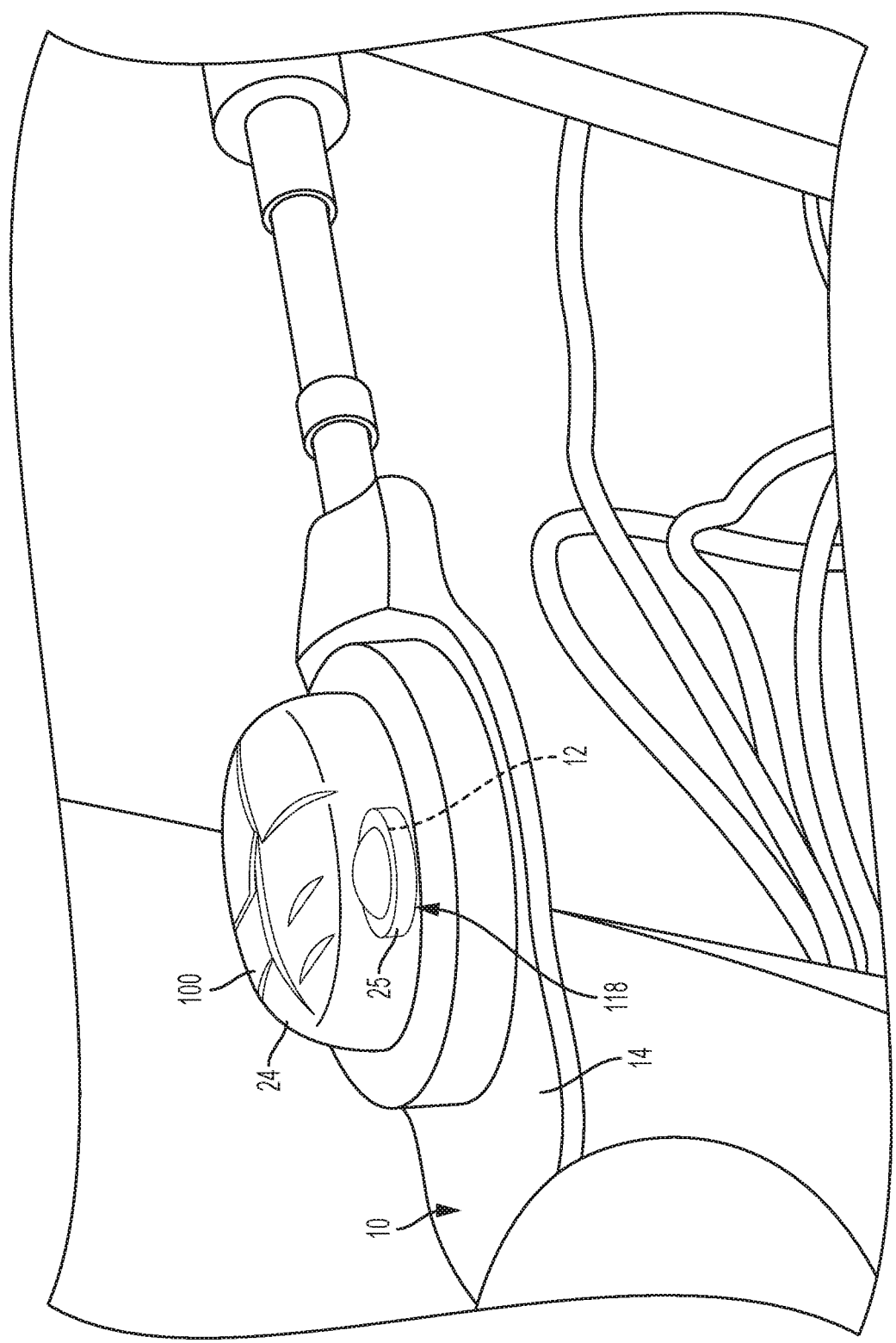
FIG. 23 is a perspective view of a sixth step of using a device of the present disclosure in accordance with an embodiment of the present invention.

After all the air has been exited from the biological fluid collection device 10 and the plugs 27 have been wetted, the remaining vacuum created by the actuator 24 pulls the upper film 25 upwards, i.e., the remaining vacuum transitions the upper film 25 from the initial position to a fill position. Referring to FIGS. 17 and 23, as the upper film 25 rises or is pulled up by the remaining vacuum (because there is no air within the biological fluid collection device 10), a portion of the blood sample 12 is drawn into a chamber 118 that is located between the inferior surface 110 of the upper film 25 and the superior surface 64 of the cavity 62. The blood sample 12 enters the chamber 118 via a slot 74 within the middle channel 72 of the sacrificial flow channel 70. The remaining vacuum pulls the upper film 25 up until the chamber 118 is filled with a blood sample 12.

The flow path of a blood sample 12 that enters into the chamber 118 is as follows. A blood sample 12 enters the biological fluid collection device 10 via the inlet 58 at the proximal end 11 then flows through an inlet flow channel 68 to the middle channel 72 and through the slot 74 into the chamber 118 of the upper film 25.

In one embodiment, as discussed above, the biological fluid collection device 10 contains an anticoagulant 23. For example, the anticoagulant 23 may be added to a blood sample 12 as the blood sample 12 flows within the inlet flow channel 68 of the biological fluid collection device 10. In one embodiment, the biological fluid collection device 10 may include a material 130 having pores 132 that may include the anticoagulant 23. In one embodiment, the material 130 is treated with an anticoagulant to form a dry anticoagulant powder finely distributed throughout the pores 132 of the material 130. As a blood sample 12 flows through the material 130 within the biological fluid collection device 10, the blood sample 12 is exposed to the anticoagulant powder throughout the internal micro pore structure of the material 130. In this manner, the biological fluid collection device 10 provides fast mixing of a blood sample 12 with an anticoagulant to produce a stabilized blood sample.

Once the chamber 118 is filled with a blood sample 12, a blood collection device attached to the biological fluid collection device 10 can be removed.

Next, when desired, the biological fluid collection device 10 can be used to dispense the blood sample 12 from the biological fluid collection device 10. In one embodiment, the stabilized blood sample may be transferred to a diagnostic instrument such as a blood testing device, a point-of-care testing device, or similar analytical device.

Referring to FIG. 24, the biological fluid collection device 10 can be used to dispense the blood sample 12 from the biological fluid collection device 10 to a point-of-care testing device or blood testing device 300. For example, the dispensing tip 57 may be positioned adjacent a receiving port 302 of the point-of-care testing device 300 for transfer of at least a portion of the blood sample 12 from the biological fluid collection device 10 to the point-of-care testing device 300.

To dispense a blood sample 12 from the biological fluid collection device 10, the button portion 100 of the actuator 24 is depressed a second time thereby providing a force to expel a blood sample out the chamber 118 of the biological fluid collection device 10. The actuator 24 can be used to dispense a blood sample 12 at a controlled rate and to dispense multiple drops of a blood sample 12 from the biological fluid collection device 10.

The flow path of a blood sample 12 that exits the chamber 118 is as follows. A blood sample 12 exits the chamber 118 of the biological fluid collection device 10 via the outlet flow channel 80 and the dispensing tip 57 at the distal end 56.

The biological fluid collection device 10 only dispenses a blood sample 12 that is contained within the chamber 118. The biological fluid collection device 10 does not dispense any portions of the blood sample 12 that are contained within the arcuate channels 76, 78 and the plugs 27 of the sacrificial flow channel 70. Once the plugs 27 are wetted they become a dead end and the blood contained within the arcuate channels 76, 78 and the plugs 27 of the sacrificial flow channel 70 become trapped. The sacrificial flow channel 70 provides a fluid path away from the dispensing channel of the biological fluid collection device 10.

Referring to FIG. 6, the biological fluid collection device 10 includes a first valve 28 and a second valve 29. In one embodiment, the first valve 28 is positioned within the first valve receiving aperture 84 of the lower housing 22 of the biological fluid collection device 10. In one embodiment, the second valve 29 is positioned within the second valve receiving aperture 86 of the lower housing 22 of the biological fluid collection device 10.

The first valve 28 is disposed in a portion of the inlet flow channel 68 between the inlet 58 and the chamber 118 and the second valve 29 is disposed in a portion of the outlet flow channel 80 between the chamber 118 and the outlet 60.

The first valve 28 is adjacent the proximal end 11 of the biological fluid collection device 10. In one embodiment, the first valve 28 is a one-way valve. The first valve 28 ensures that when the actuator 24 is depressed to create a vacuum that no air is expelled out the inlet 58 at the proximal end 11 of the biological fluid collection device 10. With the biological fluid collection device 10 connected to a blood collection device that is secured to a patient, the first valve 28 ensures that when the actuator 24 is depressed to create a vacuum that no air is aspirated into the patient. Additionally, the first valve 28 ensures that when the actuator 24 is depressed to expel a portion of the blood sample 12 from the biological fluid collection device 10 that the blood sample 12 is only able to flow out the dispensing tip 57 and that the blood sample 12 is not able to flow out the inlet 58 at the proximal end 11 of the biological fluid collection device 10.

The second valve 29 is adjacent the distal end 15 of the biological fluid collection device 10. In one embodiment, the second valve 29 is a one-way valve. The second valve 29 ensures that when the actuator 24 is depressed to expel a portion of the blood sample 12 from the biological fluid collection device 10 that no air is sucked back into the blood sample 12 and/or the biological fluid collection device 10. Additionally, the second valve 29 allows for the dispensing of a blood sample 12 from the biological fluid collection device 10 to be controlled. For example, the second valve 29 allows the blood sample 12 to be dispensed at a specific rate and allows multiple drops of a controlled size to be dispensed from the biological fluid collection device 10.

In one embodiment, the biological fluid collection device 10 may include a slow venting feature that allows the actuator 24 to fully restore to its original shape. Such a venting feature would allow the actuator 24 to slowly draw in air from the atmosphere at a much slower rate than the biological fluid collection device 10 collects a sample. By ensuring the actuator's vent is slower than the fill time, the biological fluid collection device 10 will always fill before the vacuum is exhausted. In some embodiments, this vent may simply be a small pin hole or a more advanced valve. In one embodiment, the actuator 24 may include a vent hole 104. In other embodiments, other portions of the biological fluid collection device 10 may include a vent hole.

FIGS. 27-33 illustrate other exemplary embodiments. The embodiments illustrated in FIG. 27 includes similar components to the embodiment illustrated in FIGS. 1-6, and the similar components are denoted by a reference number followed by the letter A. The embodiment illustrated in FIGS. 28-29 also includes similar components to the embodiment illustrated in FIGS. 1-6, and the similar components are denoted by a reference number followed by the letter B. For the sake of brevity, these similar components and the similar steps of using biological fluid collection device 10A (FIG. 27) and biological fluid collection device 10B (FIGS. 28-29) will not all be discussed in conjunction with the embodiments illustrated in FIG. 27 and FIGS. 28-29.

FIGS. 30-33 illustrate another exemplary embodiment. Referring to FIGS. 30-33, a biological fluid collection device 400 of the present disclosure can have a generally cylindrical shape 402. For example, in such an embodiment, an actuator 401 of the biological fluid collection device 400 does not extend beyond an exterior wall 403 of the biological fluid collection device 400. In this manner, the biological fluid collection device 400 has a tube architecture that can easily be compatible with and fit into a holder 404 as shown in FIGS. 31 and 32.

Figure 25:
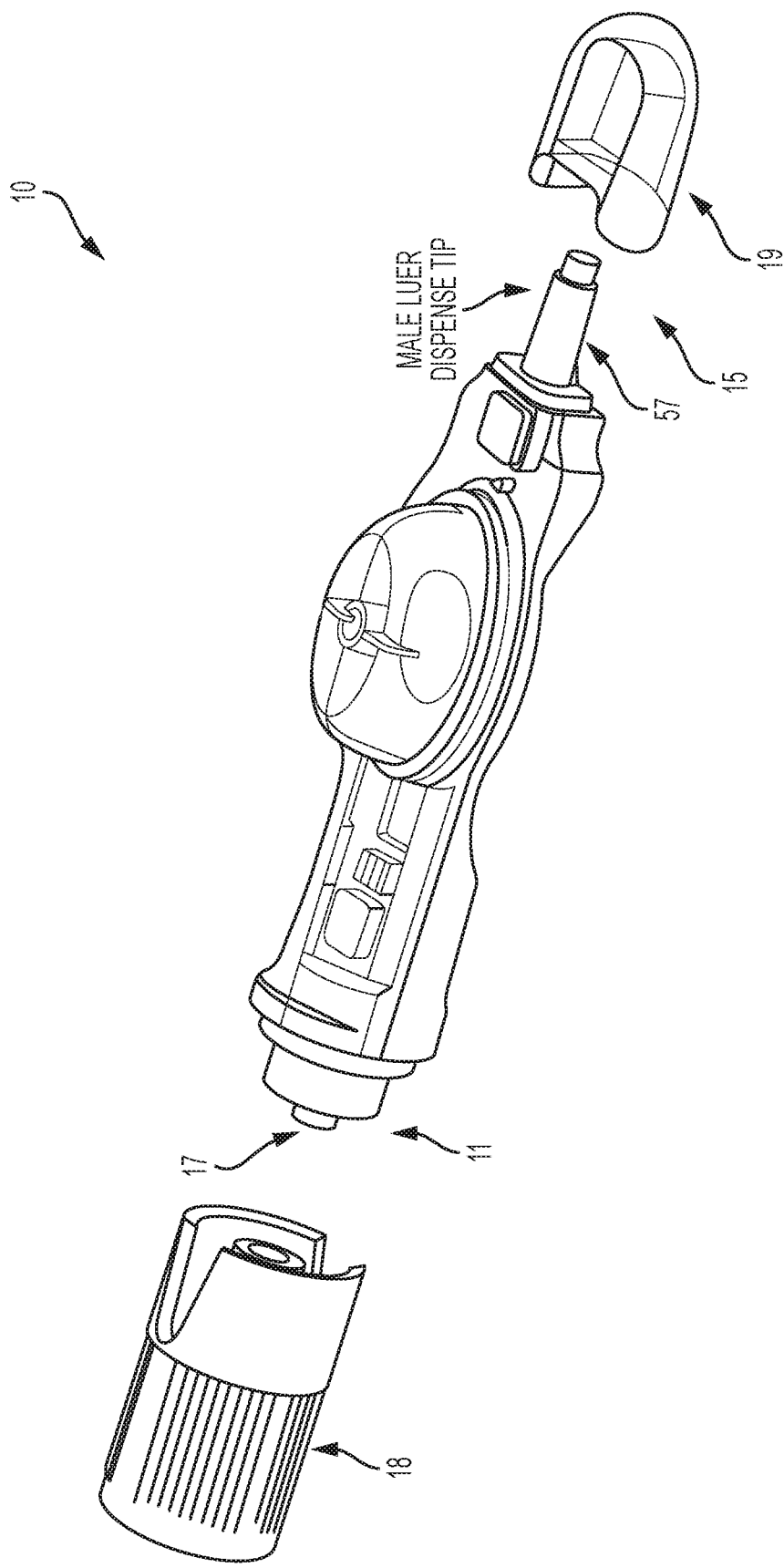
FIG. 25 is an exploded, perspective view of a superior surface of a biological fluid collection device in accordance with an embodiment of the present invention.
Figure 26:
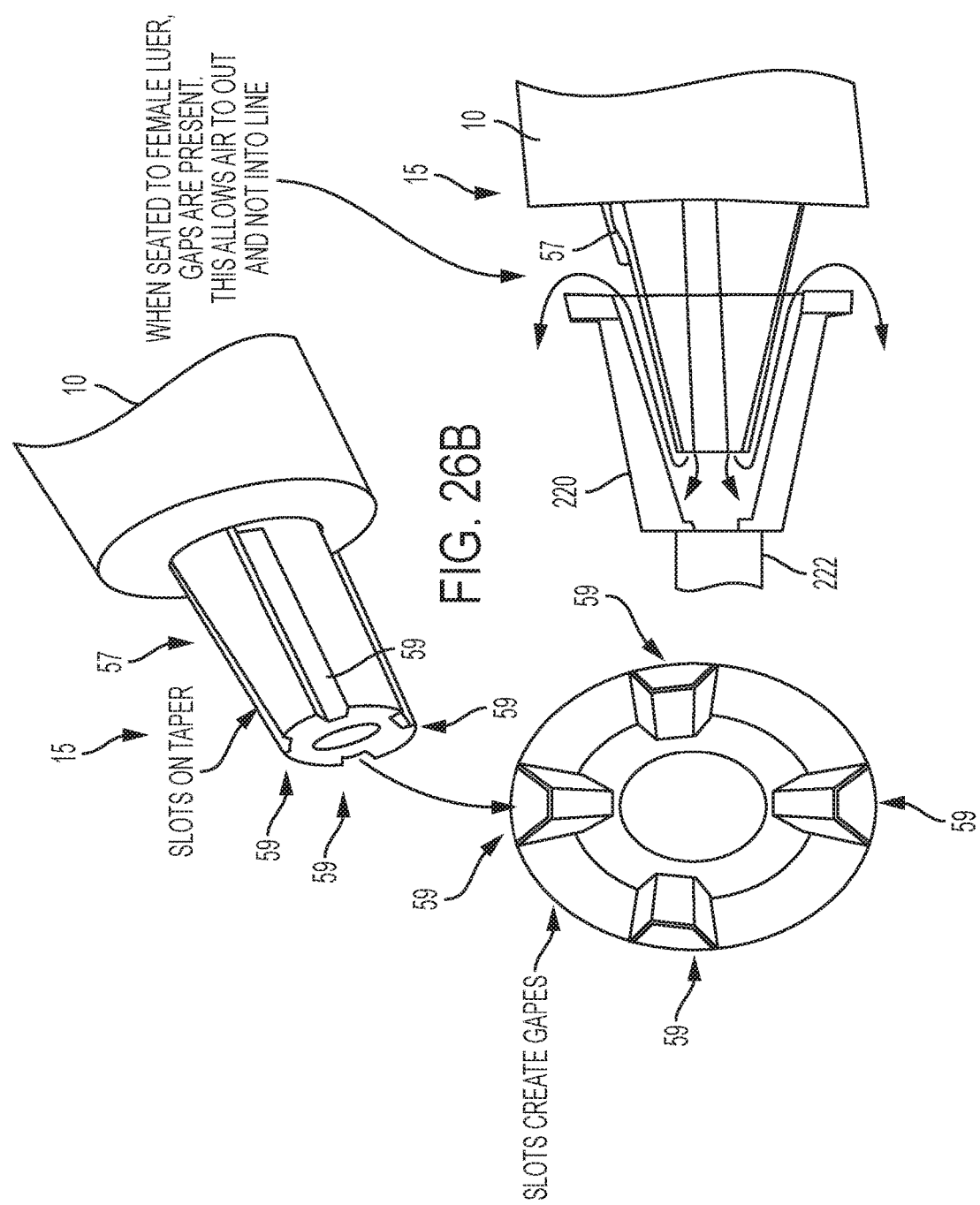
FIG. 26A is an elevation view of a distal end of a biological fluid collection device in accordance with an embodiment of the present invention.
FIG. 26B is a perspective view of a distal end of a biological fluid collection device in accordance with an embodiment of the present invention.
FIG. 26C is a cross-sectional view of a distal end of a biological fluid collection device engaged with a luer connector in accordance with an embodiment of the present invention.
Figure 36:
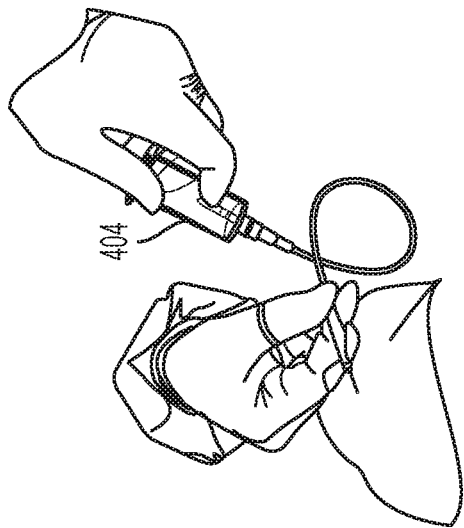
FIG. 36 is a perspective view of a third step of using a device of the present disclosure in accordance with an embodiment of the present invention.
Figure 38:
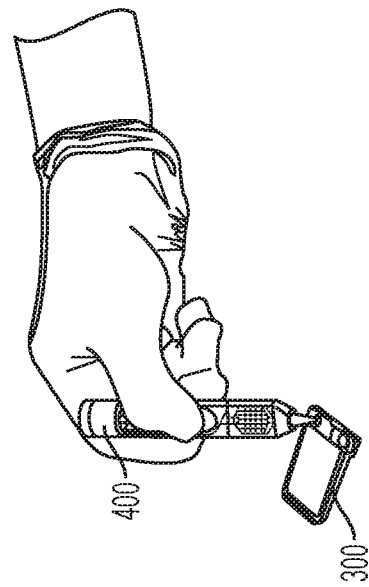
FIG. 38 is a perspective view of a fifth step of using a device of the present disclosure in accordance with an embodiment of the present invention.
Figure 34:
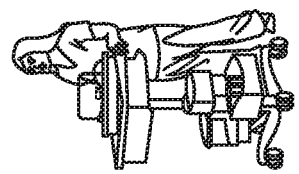
FIG. 34 is a perspective view of a first step of using a device of the present disclosure in accordance with an embodiment of the present invention.
Figure 35:
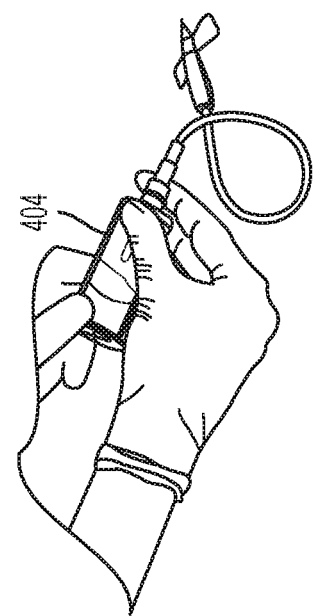
FIG. 35 is a perspective view of a second step of using a device of the present disclosure in accordance with an embodiment of the present invention.
Figure 37:
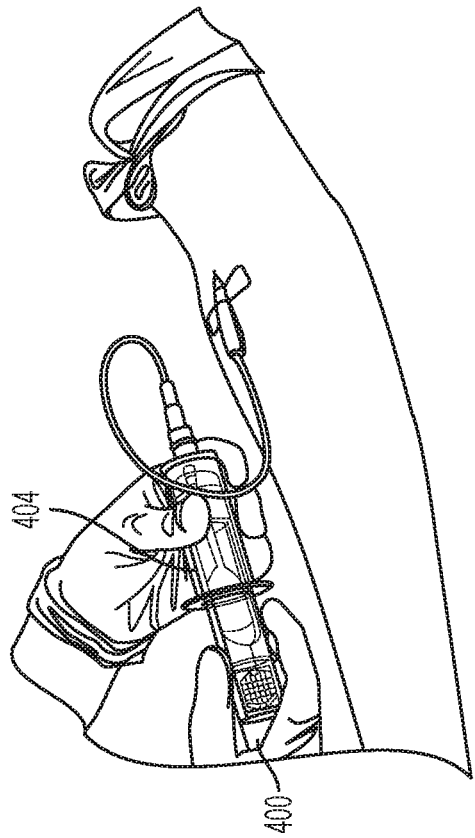
FIG. 37 is a perspective view of a fourth step of using a device of the present disclosure in accordance with an embodiment of the present invention.

Referring to FIGS. 25-26C, the distal end 15 of the biological fluid collection device 10 includes a plurality of slots 59. For example, the dispensing tip 57 includes a plurality of slots 59.

The slots 59 provide a safety feature such that if the wrong end of the biological fluid collection device 10 is connected with a blood collection device, i.e., if the distal end 15 is connected with a blood collection device, and the actuator 24 is depressed, air is prevented from being expelled to a patient. The slots 59 ensure that no hermetic seal is created with a connection to a blood collection device. For example, referring to FIG. 26C, if the distal end 15 of the biological fluid collection device 10 is connected with a luer fitting 220 of a blood collection device, the slots 59 provide gaps that allow air to leak out and not move through a line 222. In this manner, the slots 59 prevent air from being expelled into a patient. Any air is vented out to atmosphere via the slots 59 before entering a line 222.

In other embodiments, the distal end 15 of the biological fluid collection device 10 can include other venting mechanisms. For example, the distal end 15 of the biological fluid collection device 10 can include a rough finish that inhibits a proper seal, a valve mechanism, a keyed mechanism, or other mechanisms that prevent a hermetic seal with a blood collection device so that any air is vented out to atmosphere before entering a line 222.

The slots 59 do not inhibit a secure, physical connection to a Luer connector. A secure Luer interface via the distal end 15 of the biological fluid collection device 10 can be used to connect to some blood analyzers, blood testing devices, or other devices.

A biological fluid collection device of the present disclosure provides a device that can connect to a line or a tube holder to receive a blood sample. A vacuum is created by activating an energy source to evacuate air and pull in a blood sample. The energy source of a biological fluid collection device of the present disclosure can be any means to create a vacuum. A sample stabilizer, such as an anticoagulant, can be added to the blood as it flows in the biological fluid collection device. In this manner, the blood picks up and mixes with the anticoagulant as it passes through the biological fluid collection device.

In some embodiments, a visual indicator can show a red color when collection of a blood sample is complete. In one embodiment, the visual indicator can comprise a transparent surface in a portion of the housing of the biological fluid collection device. After a blood sample is collected within the biological fluid collection device, the biological fluid collection device can be removed from the site of collection and/or any blood collection device. The transfer or dispensing of a stabilized blood sample from the biological fluid collection device can be accomplished by an end user. The user can remove an end cap and transfer a stabilized blood sample into a blood testing device by depressing an actuator. The actuator is capable of allowing a blood sample to be dispensed and/or transferred at a specific rate.

The plugs 27 and the sacrificial flow channel 70 allow the biological fluid collection device 10 to vent air as if fills with blood (anaerobic blood collection). Without a venting feature, the biological fluid collection device 10 would have a mixture of blood and air. Having blood and air in the device's fluid path could potentially skew air blood gas (ABG) readings of the sample.

The upper film 25, the plugs 27, and the sacrificial flow channel 70 allow automatic anaerobic collection of blood. Users of conventional devices, such as syringes, have to burp a syringe into gauze to evacuate air from a collected sample. Additionally, the plugs 27 and the sacrificial flow channel 70 offer a long fluid path away from the dispensing channel. This distance is important to prevent and avoid any analyte bias of a blood sample dispensed from the biological fluid collection device 10. The blood in the plugs 27 and the sacrificial flow channel 70 does not get dispensed.

A biological fluid collection device of the present disclosure may include a transfer tip that is capped or concealed in some manner. For example, the transfer tip can be a Male luer with a one way valve. This allows it to interface with cartridge inlets in a direct fit. Also, the Male luer allows for a compatible interface with near patient testing instruments such as ABG (arterial blood gas) instruments. They have a male luer connection for direct connection and interface.

This compatibility is an advantage and allows for multiple applications of a biological fluid collection device of the present disclosure.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection device, comprising:
   a housing having a superior surface, an inferior surface, a proximal end, a distal end, an inlet channel, and an outlet channel, wherein a portion of the superior surface of the housing defines a cavity having a cavity superior surface, and wherein a portion of the inferior surface of the housing defines a sacrificial flow channel, the sacrificial flow channel comprising:
      a middle channel having a first middle channel end, a second middle channel end, and defining a slot, the first middle channel end in fluid communication with the inlet channel, the middle channel extending from the inlet channel in a first direction;
      a first arcuate channel having a first arcuate channel distal end and a first arcuate channel proximal end, the first arcuate channel distal end in communication with the second middle channel end, the first arcuate channel extending from the second middle channel end in a second direction; and
      a second arcuate channel having a second arcuate channel distal end and a second arcuate channel proximal end, the second arcuate channel distal end in communication with the second middle channel end, the second arcuate channel extending from the second middle channel end in the second direction;
   a first venting plug disposed in the first arcuate channel proximal end;
   a second venting plug disposed in the second arcuate channel proximal end; and
   an actuator for creating a vacuum for drawing a blood sample into the housing,
   wherein each of the first arcuate channel and the second arcuate channel are in communication with the inlet channel but are spaced apart from the inlet channel by the middle channel.

2. The biological fluid collection device of claim 1, further comprising a film engageable with the housing, the film having a film inferior surface and a film superior surface, the film transitionable between an initial position in which the film inferior surface is in contact with the cavity superior surface and a fill position in which the film inferior surface is spaced from the cavity superior surface forming a chamber between the film and the housing, wherein the chamber is in fluid communication with the middle channel via the slot.

3. The biological fluid collection device of claim 2, wherein the actuator is disposed at least partially within the housing and in communication with the film and the housing, the actuator transitionable between an original position and a depressed position,
   wherein after actuation of the actuator to the depressed position, as the actuator returns to the original position, the actuator simultaneously applies a vacuum to the film superior surface and to the inferior surface of the housing.

4. The biological fluid collection device of claim 2, wherein the chamber is in fluid communication with the outlet channel.

5. The biological fluid collection device of claim 1, wherein the second direction is substantially opposite the first direction.

6. The biological fluid collection device of claim 1, wherein the first arcuate channel extends in the second direction away from the second middle channel end towards the first middle channel end.

7. The biological fluid collection device of claim 1, wherein the second arcuate channel extends in the second direction away from the second middle channel end towards the first middle channel end.

8. The biological fluid collection device of claim 1, wherein the first arcuate channel and the second arcuate channel are on opposing sides of the middle channel.

9. The biological fluid collection device of claim 1, wherein the biological fluid collection device is for anaerobic blood collection of the blood sample.

* * * * *